United States Patent
Porto et al.

(10) Patent No.: US 8,343,135 B2
(45) Date of Patent: Jan. 1, 2013

(54) ANTI-MICROBIAL CATHETER

(75) Inventors: James Dal Porto, Coto de Caza, CA (US); Jose Castillo Deniega, Lake Forest, CA (US); Roger Massengale, Mission Viejo, CA (US); Kenneth W. Rake, Laguna Niguel, CA (US); Lois Rake, legal representative, Laguna Niguel, CA (US); Kevin Forest, Rancho Santa Margarita, CA (US); Mark Siminuk, Lake Forest, CA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/415,304

(22) Filed: Mar. 31, 2009
(Under 37 CFR 1.47)

(65) Prior Publication Data

US 2009/0187152 A1 Jul. 23, 2009

Related U.S. Application Data

(63) Continuation of application No. 11/216,534, filed on Aug. 31, 2005, now Pat. No. 7,547,302, which is a continuation-in-part of application No. 10/436,457, filed on May 12, 2003, now Pat. No. 7,452,353, and a continuation-in-part of application No. 10/435,946, filed on May 12, 2003, now Pat. No. 7,510,550, said application No. 10/436,457 is a continuation-in-part of application No. 10/031,913, filed as application No. PCT/US00/19746 on May 21, 2002, now Pat. No. 7,780,638, said application No. 10/435,946 is a continuation-in-part of application No. 10/031,913, filed as application No. PCT/US00/19746 on May 21, 2002, now Pat. No. 7,780,638, which is a continuation-in-part of application No. 09/363,228, filed on Jul. 19, 1999, now Pat. No. 6,350,253.

(51) Int. Cl.
A61M 25/00 (2006.01)
(52) U.S. Cl. .................................................. 604/523
(58) Field of Classification Search .................. 604/523, 604/10, 22, 93.01, 269, 508, 131, 164.01, 604/171, 264
See application file for complete search history.

(56) References Cited

U.S. PATENT DOCUMENTS 623,022 A * 4/1899 Johnson ..................... 607/116
(Continued)

FOREIGN PATENT DOCUMENTS

DE 3400874 C1 2/1985
(Continued)

*Primary Examiner* — Nicholas Lucchesi
*Assistant Examiner* — Brooke Matney
(74) *Attorney, Agent, or Firm* — Dority & Manning, P.A.

(57) ABSTRACT

A catheter having features configured to provide a substantially uniform flow rate of a fluid exiting the catheter and also exhibits anti-microbial properties. The uniform flow rate features may include one or more of a flow restricting membrane or flow restricting component within an infusion section of the catheter. In other arrangements, exit holes defining the infusion section of the catheter may be configured to provide the desired uniform flow rate over the length of the infusion section. Furthermore, the catheter also includes anti-microbial properties to inhibit the growth of microbes on or within the catheter and, preferably, to inhibit microbe growth in an anatomical region surrounding the catheter. The desired anti-microbial properties may be provided by an anti-microbial layer, anti-microbial materials dispersed within the material from which components of the catheters are constructed, or a combination of anti-microbial layers and embedded anti-microbial materials. In some arrangements, one or more portions of the catheter may be bio-absorbable.

15 Claims, 9 Drawing Sheets

U.S. PATENT DOCUMENTS

| | | | |
|---|---|---|---|
| 3,595,241 | A | 7/1971 | Sheridan |
| 3,821,956 | A | 7/1974 | Gordhamer |
| 3,841,308 | A | 10/1974 | Tate |
| 3,938,529 | A | 2/1976 | Gibbons |
| 4,054,139 | A | 10/1977 | Crossley |
| 4,141,379 | A | 2/1979 | Manske |
| 4,182,343 | A | 1/1980 | Inaba |
| 4,753,640 | A | 6/1988 | Nichols et al. |
| 4,826,485 | A | 5/1989 | Johnson |
| 4,954,388 | A | 9/1990 | Mallouk et al. |
| 4,976,689 | A | 12/1990 | Buchbinder et al. |
| 4,985,022 | A | 1/1991 | Fearnot et al. |
| 4,999,210 | A | 3/1991 | Solomon et al. |
| 5,021,044 | A | 6/1991 | Sharkawy |
| 5,032,113 | A | 7/1991 | Burns |
| 5,066,278 | A | 11/1991 | Hirschberg et al. |
| 5,069,674 | A | 12/1991 | Fearnot et al. |
| 5,129,889 | A | 7/1992 | Hahn et al. |
| 5,146,916 | A | 9/1992 | Catalani |
| 5,184,627 | A | 2/1993 | De Toledo |
| 5,201,723 | A | 4/1993 | Quinn |
| 5,201,724 | A | 4/1993 | Hukins et al. |
| 5,213,576 | A | 5/1993 | Abiuso et al. |
| 5,250,034 | A * | 10/1993 | Appling et al. .......... 604/164.02 |
| 5,267,979 | A | 12/1993 | Appling et al. |
| 5,269,755 | A | 12/1993 | Bodicky |
| 5,273,875 | A | 12/1993 | Griffith |
| 5,344,412 | A | 9/1994 | Wendell et al. |
| 5,356,388 | A | 10/1994 | Sepetka et al. |
| 5,376,083 | A | 12/1994 | Mische |
| 5,401,257 | A | 3/1995 | Chevalier, Jr. et al. |
| 5,405,316 | A | 4/1995 | Magram |
| 5,425,723 | A | 6/1995 | Wang |
| 5,441,481 | A | 8/1995 | Mishra et al. |
| 5,458,570 | A | 10/1995 | May, Jr. |
| 5,458,582 | A | 10/1995 | Nakao |
| 5,536,261 | A | 7/1996 | Stevens |
| 5,569,219 | A | 10/1996 | Hakki et al. |
| 5,609,583 | A | 3/1997 | Hakki et al. |
| 5,624,392 | A | 4/1997 | Saab |
| 5,643,228 | A | 7/1997 | Schucart et al. |
| 5,702,372 | A | 12/1997 | Nelson |
| 5,709,874 | A | 1/1998 | Hanson et al. |
| 5,718,712 | A | 2/1998 | Bonnal et al. |
| 5,776,111 | A | 7/1998 | Tesio |
| 5,776,115 | A | 7/1998 | Antoshkiw et al. |
| 5,800,407 | A | 9/1998 | Eldor |
| 5,800,408 | A | 9/1998 | Strauss et al. |
| 5,817,072 | A | 10/1998 | Lampropoulos et al. |
| 5,833,652 | A | 11/1998 | Preissman et al. |
| 5,843,050 | A | 12/1998 | Jones et al. |
| 5,846,216 | A | 12/1998 | Gonzales et al. |
| 5,876,376 | A | 3/1999 | Schwab et al. |
| 5,891,101 | A | 4/1999 | Wilcox et al. |
| 5,891,154 | A | 4/1999 | Loeffler |
| 5,947,940 | A | 9/1999 | Beisel |
| 5,957,899 | A | 9/1999 | Spears et al. |
| 5,957,901 | A * | 9/1999 | Mottola et al. ................ 604/264 |
| 6,004,279 | A | 12/1999 | Crowley et al. |
| 6,022,602 | A | 2/2000 | Nomura |
| 6,053,932 | A | 4/2000 | Daniel et al. |
| 6,070,575 | A * | 6/2000 | Gonda et al. ............. 128/203.12 |
| 6,093,180 | A | 7/2000 | Elsberry |
| 6,123,688 | A | 9/2000 | Biotich et al. |
| 6,128,537 | A | 10/2000 | Rise |
| 6,179,816 | B1 | 1/2001 | Mottola et al. |
| 6,183,461 | B1 | 2/2001 | Matsuura et al. |
| 6,206,849 | B1 | 3/2001 | Martin et al. |
| 6,210,395 | B1 | 4/2001 | Fleischhacker et al. |
| 6,235,007 | B1 | 5/2001 | Divino, Jr. et al. |
| 6,273,875 | B1 * | 8/2001 | Siman et al. .................. 604/264 |
| 6,280,788 | B1 | 8/2001 | Rakhorst et al. |
| 6,290,689 | B1 | 9/2001 | Delaney et al. |
| 6,333,093 | B1 * | 12/2001 | Burrell et al. ................. 428/194 |
| 6,350,253 | B1 | 2/2002 | Deniega et al. |
| 6,537,194 | B1 | 3/2003 | Winkler |
| 6,537,241 | B1 | 3/2003 | Odland |
| 6,623,449 | B2 | 9/2003 | Paskar |
| 6,676,643 | B2 | 1/2004 | Brushey |
| 7,004,923 | B2 | 2/2006 | Deniega et al. |
| 2001/0027599 | A1 | 10/2001 | Elsberry |
| 2002/0082547 | A1 | 6/2002 | Deniega et al. |
| 2003/0036728 | A1 | 2/2003 | Samson et al. |
| 2003/0158538 | A1 | 8/2003 | Deniega et al. |
| 2003/0181864 | A1 | 9/2003 | Deniega et al. |
| 2004/0064129 | A1 | 4/2004 | Deniega et al. |
| 2006/0149192 | A1 | 7/2006 | Deniega et al. |

FOREIGN PATENT DOCUMENTS

| | | |
|---|---|---|
| DE | 44 02 475 A1 | 3/1995 |
| EP | 0 804 936 | 11/1997 |
| FR | 2 539 298 | 1/1983 |
| FR | 2 622 805 | 11/1987 |
| GB | 2 277 035 | 10/1994 |
| GB | 2332 493 A | 6/1999 |
| JP | 4 327857 | 11/1992 |
| WO | WO 90/12611 | 11/1990 |
| WO | WO 92/00113 | 1/1992 |
| WO | WO 92/11895 | 7/1992 |
| WO | WO 93/14350 | 9/1993 |
| WO | WO 94/01160 A1 | 1/1994 |
| WO | WO 96/07445 A1 | 3/1996 |
| WO | WO 96/16685 | 6/1996 |
| WO | WO 96/16690 | 6/1996 |
| WO | WO 96/33761 | 10/1996 |
| WO | WO 97/49447 | 12/1997 |
| WO | WO 01/43788 A3 | 6/2001 |
| WO | WO 03/009883 A2 | 2/2003 |
| WO | WO 2004/101052 | 11/2004 |

* cited by examiner

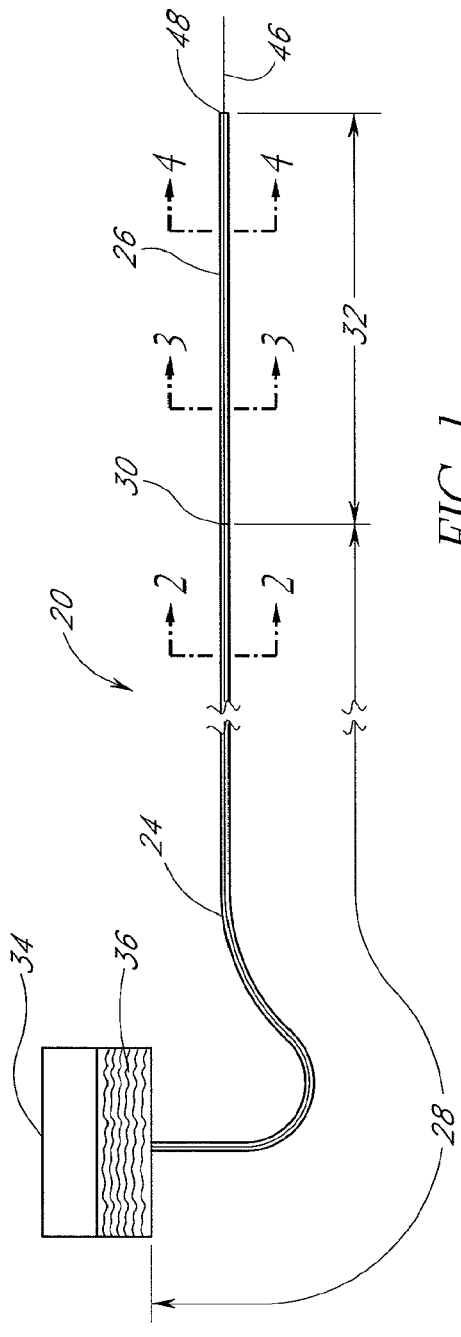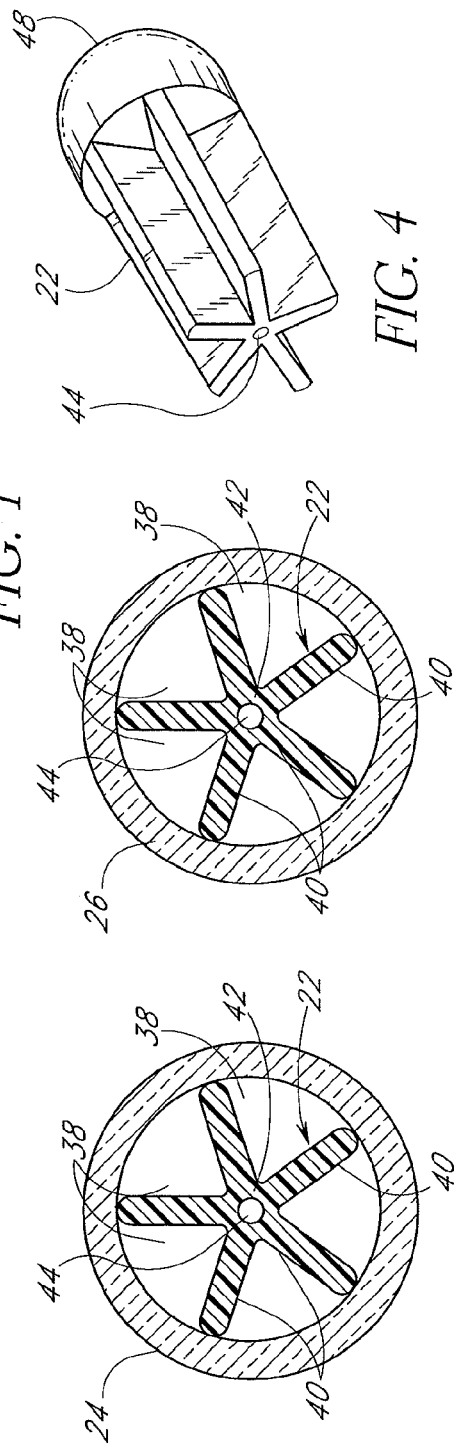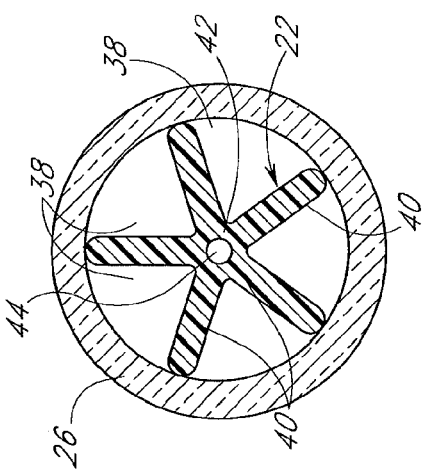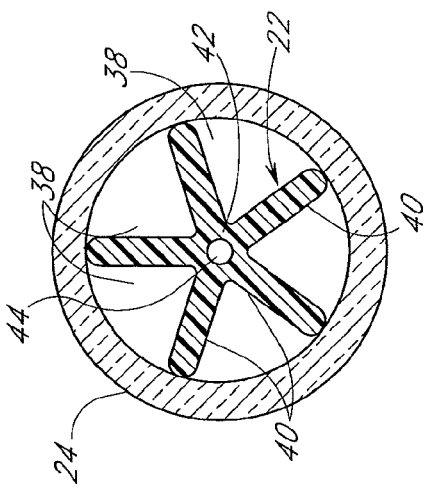

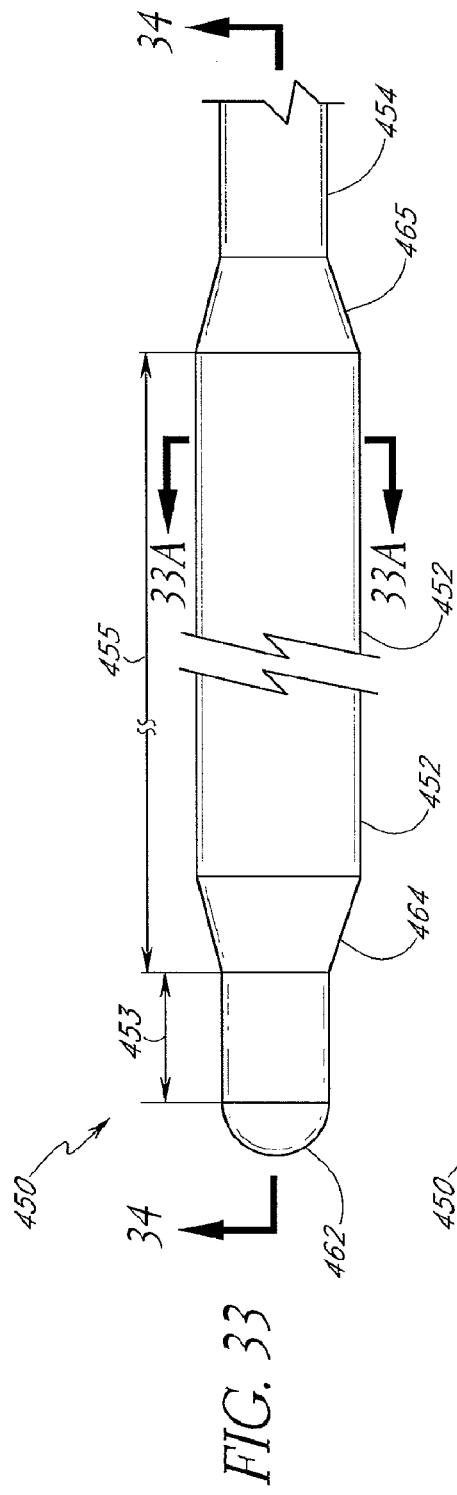

ANTI-MICROBIAL CATHETER

RELATED APPLICATIONS

This application is a continuation of U.S. patent application Ser. No. 11/216,534, filed Aug. 31, 2005, which is a continuation-in-part of U.S. patent application Ser. No. 10/436,457, filed May 12, 2003, now U.S. Pat. No. 7,452,353, and U.S. patent application Ser. No. 10/435,946, filed May 12, 2003, which are continuations-in-part of U.S. patent application Ser. No. 10/031,913, filed May 21, 2002, which is a U.S. National Phase of International Patent Application No. PCT/US00/19746, filed Jul. 19, 2000 and published in English, which is a continuation-in-part U.S. patent application Ser. No. 09/363,228, filed Jul. 19, 1999, now U.S. Pat. No. 6,350,253, the entireties of which are hereby incorporated by reference herein and made a part of the present disclosure.

BACKGROUND OF THE INVENTION

1. Field of the Invention

This invention generally relates to catheters and, in particular, to a catheter that exhibits anti-microbial properties and delivers fluid medication uniformly across an infusion section of the catheter.

2. Description of the Related Art

Infusion catheters for delivery of fluid medication into anatomical systems, such as the human body, are well known in the art. Such catheters generally include a flexible hollow tube inserted into some region of the anatomy. The tube typically contains one or more axial lumens within which the fluid may flow. The proximal end of the catheter tube is connected to a fluid source from which fluid is introduced into the catheter tube. The fluid flows within one of the lumens under pressure supplied at the proximal end of the tube. For each lumen, there are commonly provided one or more exit holes along an infusion section near the distal end of the tube, for fluid to exit the tube. Such exit holes are created by piercing the side wall of the hollow tube.

In certain medical conditions, it is advantageous to deliver fluid medication to a plurality of sites within a wound area. For instance, some wounds which require pain medication may be in communication with many nerve endings, rather than a single nerve trunk. One example of such a wound is a surgical incision. As stated above, it is known to provide a plurality of exit holes through which the fluid medication exits the catheter tube. The exit holes may be provided at various axial and circumferential positions along the catheter tube in order to control the position of the medication delivery sites. An example of a catheter having this configuration is disclosed in U.S. Pat. No. 5,800,407 to Eldor. Also, in some cases it is desirable to deliver such medication under low pressure, so that the fluid is delivered at a relatively low rate. For example, some pain medications must be delivered slowly to avoid toxicity and other side effects. Furthermore, in many cases it is desirable to dispense fluid medication at a substantially uniform rate throughout the infusion section of the catheter, so that the medication is evenly distributed throughout the wound area.

Unfortunately, a limitation of prior art catheters with multiple exit holes, such as the catheter taught by Eldor, is that during low pressure delivery of fluid medication the fluid tends to exit only through the exit hole(s) nearest to the proximal end of the infusion section of the catheter tube. This is because fluids flowing through a tube more readily exit through the exit holes offering the least flow resistance. The longer the flow path followed by the fluid in the lumen, the higher the flow resistance and pressure drop experienced by the fluid. The most proximal holes offer the least flow resistance and pressure drop. Therefore, the fluid tends to exit the catheter tube primarily through these exit holes. As a result, the fluid medication is delivered only to a small region within the wound area. The tendency of the fluid to undesirably flow only through the most proximal exit holes depends upon the hole size, the total number of exit holes, and the flow rate. As the hole size or number of holes increases, the fluid becomes more likely to exit only through the most proximal holes. Conversely, as the flow rate increases, the fluid becomes less likely to do so.

The tendency of the fluid to undesirably exit only through the most proximal holes of the catheter can in some cases be overcome by increasing the flow rate or pressure of the fluid, which causes the fluid to flow through more of the exit holes of the catheter. Indeed, if the flow rate or pressure is sufficiently high, the fluid will flow through all of the exit holes. However, sometimes it is medically desirable to deliver medication at a relatively slow rate, i.e., at a low pressure. Also, even in those cases in which high pressure fluid delivery is acceptable or desirable, prior art catheters do not provide for uniform fluid delivery along the infusion section of the catheter. Rather, the flow rate through the exit holes nearer to the proximal end of the infusion section tends to be greater than that through the exit holes nearer to the distal end. This is because the fluid passing through the more proximal holes experiences a lower flow resistance and pressure drop. In contrast, the fluid flowing through the more distal holes experiences greater flow resistance and pressure drop, and consequently exits at a lower flow rate. The further distal the hole, the lower the exit flow rate of the fluid. As a result, there is an uneven distribution of medication throughout the wound area.

In another known type of infusion catheter, several lumens are provided within a catheter tube. For each lumen, one exit hole is provided by piercing a hole within the wall of the tube. The exit holes are provided at different axial positions along the infusion section of the catheter tube. In this manner, fluid medication may be delivered to several positions within the wound area. While this configuration offers improved fluid distribution, it has some disadvantages. One disadvantage is that the fluid flow rates through the exit holes are not equal, since the more distal exit holes offer a greater flow resistance for the same reasons discussed above. Another disadvantage is that the number of lumens, and consequently the number of fluid exit holes, is limited by the small diameter of the catheter tube. As a result, fluid may be delivered only to a very limited number of positions within the wound area. Yet another disadvantage is that the proximal ends of the lumens must be attached to a complicated manifold which increases the cost of manufacturing the catheter.

An example of a catheter providing a more uniform dispensation of fluid medication throughout an infusion section of the catheter is illustrated by U.S. Pat. No. 5,425,723 to Wang. Wang discloses an infusion catheter including an outer tube, an inner tube concentrically enclosed within the outer tube, and a central lumen within the inner tube. The inner tube has a smaller diameter than the outer tube, so that an annular passageway is formed therebetween. The outer tube has a plurality of evenly spaced exit holes defining the infusion section of the catheter. In use, fluid flowing within the central lumen passes through strategically positioned side holes within the side walls of the inner tube. In particular, the spacing between adjacent side holes decreases along a length of the inner tube to induce more fluid to pass through the more distal side holes. The fluid then flows longitudinally through the annular passageway before exiting through the exit holes in the outer tube wall. In the annular passageway, the fluid can flow in a distal or proximal direction, depending on the location of the nearest exit hole in the outer tube. This configuration is provided to induce a more uniform exit flow rate of fluid from the catheter.

Unfortunately, the Wang catheter is only effective for relatively high pressure fluid delivery. When used for relatively low pressure fluid delivery, the catheter disclosed by Wang does not provide uniform dispensation of fluid. Instead, the fluid tends to exit through the side holes of the inner and outer tubes that are nearest to the proximal end of the infusion section of the catheter, since these holes offer the least flow resistance. Even for high pressure fluid delivery, there are several limitations of this design. One limitation is that the concentric tubes design is relatively complex and difficult to manufacture. Both tubes must be flexible enough to permit maneuverability through an anatomical system, yet the annular passageway must remain open so that fluid may flow uniformly therein. Another limitation is that the annular passageway may be disturbed if there is a bend in the infusion section of the tube. A bend in the catheter may deform the annular passageway or even cause the inner and outer tubes to come into contact. This can cause an uneven fluid pressure within a longitudinal cross-section of the annular passageway, resulting in non-uniform fluid delivery.

Another problem with prior art catheters used for epidural, nerve block and wound site pain management applications is the increased potential for infection resulting from incision in the patient's skin to permit insertion of the catheter or from the mere existence of the catheter within the patient. The incision that permits the catheter to be inserted into the patient compromises the protective function of the skin and may allow microbial growth at or near the incision. In addition, the catheter itself may provide a means for microbes to enter the body and cause an infection. Typically, the area around the insertion site of the catheter is cleaned regularly and protected with a wound dressing and/or antibiotic ointment. However, this repetitive cleaning is usually uncomfortable to the patient and may not entirely prevent the occurrence of an infection.

SUMMARY OF THE INVENTION

Accordingly, preferred embodiments of the present catheter are configured to overcome some or all of these limitations and to provide an improved catheter for delivering fluid medication to an anatomical region, while also providing advantageous anti-microbial properties. Preferably, the catheters are configured to provide a sustained release of an active anti-microbial substance, such as metal ions, for example. In one preferred arrangement, the catheter includes a silver ion containing material coated on or dispersed within one or more components or portions of the catheter. In certain preferred arrangements, at least a portion of the catheter is made of a bio-absorbable material. Furthermore, the catheters may be constructed as aspiration catheters and employed to remove fluid from an anatomical region.

A preferred embodiment is a catheter for delivery of fluid including an elongated tube having a plurality of exit holes provided along a length of the tube to define an infusion section of the catheter. The tube is sized to be inserted into an anatomical region. An elongated member is positioned within the tube and is formed of a porous material configured to control a rate of fluid flow through the member. The catheter is configured such that a fluid introduced into a proximal end of the tube will flow through the exit holes. At least one of the tube and the elongated member incorporates an anti-microbial substance and is configured for the sustained release of the anti-microbial substance into the fluid.

Another preferred embodiment is a catheter for delivery of fluid including an elongated support and a porous membrane wrapped around the support. The support and the porous membrane cooperate to define at least one lumen to receive a flow of fluid. At least one of the support and the porous membrane incorporate an anti-microbial substance and is configured for the sustained release of the anti-microbial substance into the fluid.

Yet another preferred embodiment is a catheter for the delivery of fluid including a tube and a tubular coil spring having a proximal end attached to a distal end of the tube. A stop closes a distal end of the spring. The tube and the spring each define a portion of a central lumen. The spring has adjacent coils in contact with one another when the spring is in a relaxed state, so that fluid within the spring and below a threshold dispensation pressure is prevented from exiting the lumen by flowing radially between the coils. The spring has the property of stretching when the fluid pressure is greater than or equal to the threshold dispensation pressure to permit the fluid to be dispensed from the lumen by flowing radially between the coils. At least one of the tube and the tubular coil spring comprises an anti-microbial substance and is configured for the sustained release of the anti-microbial substance into the fluid.

Another preferred embodiment is a catheter for the delivery of fluid including a distally closed tube. A length of the tube defines an infusion section of the catheter and has a plurality of exit holes in a side wall of the tube. A tubular coil spring is enclosed within the infusion section so that a lumen is defined within the tube and the spring. The spring has adjacent coils in contact with one another so that fluid within the lumen and below a threshold dispensation pressure is prevented from exiting the lumen by flowing radially between the coils. The spring has the property of stretching when the fluid pressure is greater than or equal to the threshold dispensation pressure to permit the fluid to be dispensed from the lumen by flowing radially between the coils and through the exit holes. At least one of the tube and the spring incorporates an anti-microbial substance and is configured for the sustained release of the anti-microbial substance into the fluid.

Yet another preferred embodiment is a catheter for the delivery of fluid throughout an anatomical region including a tube having a closed distal end and defining an interior lumen having a minimum cross-sectional flow area. A distal end portion of the tube includes a plurality of exit holes therethrough. The plurality of exit holes are sized such that a combined flow area of the exit holes is less than the minimum cross-sectional flow area such that the exit holes form a flow-restricting orifice for the flow of a fluid from within the lumen through the exit holes. The tube incorporates an anti-microbial substance and is configured for the sustained release of the anti-microbial substance into the fluid.

Still another preferred embodiment is a catheter for delivering a fluid including an elongated tube having a closed distal end. At least a distal section of the tube is constructed from a bio-absorbable material. At least a portion of the distal section defines a porous side wall, which permits fluid within the lumen to pass through the portion of the distal section. At least a portion of the distal section incorporates an anti-microbial substance and is configured for the sustained release of the anti-microbial substance into the fluid.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiments disclosed.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

BRIEF DESCRIPTION OF THE DRAWINGS

FIG. 1 is a schematic side view of a catheter having features and advantages in accordance with a first embodiment of the present invention.

FIG. 2 is a sectional view of the catheter of FIG. 1, taken along line 2-2 of FIG. 1.

FIG. 3 is a sectional view of the catheter of FIG. 1, taken along line 3-3 of FIG. 1.

FIG. 4 is a perspective view of the end portion and support beam of the catheter of FIG. 1, illustrating a cross-section taken along line 4-4 of FIG. 1.

FIG. 33 is side elevation view of a catheter having features and advantages in accordance with another embodiment of the present invention, which includes a tubular porous membrane, or sheath.

FIG. 33A is a cross-sectional view of the catheter of FIG. 33, taken along line 33A-33A.

FIG. 34 is a cross-sectional view of the catheter of FIG. 33, taken along line 34-34.

DETAILED DESCRIPTION OF THE PREFERRED EMBODIMENTS

Figure 8:
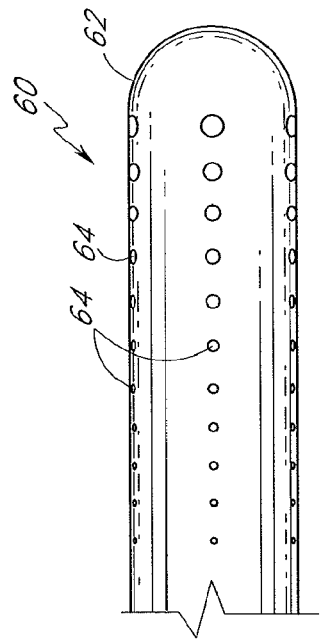
FIG. 8 is a side view of a catheter having features and advantages in accordance with a fourth embodiment of the present invention.

FIGS. 1-4 illustrate an infusion catheter 20 according to one embodiment of the present invention. Catheter 20 preferably includes a flexible support 22 (FIGS. 2-4), a non-porous membrane 24, and a porous membrane 26. The membranes 24 and 26 are wrapped around the support 22 to form a plurality of axial lumens between the inner surfaces of the membranes 24 and 26 and the surface of the support 22, as described in greater detail below. The non-porous membrane 24 defines a non-infusing section 28 of the catheter 20, and preferably covers the support 22 from the proximal end thereof to a point 30, shown in FIG. 1. Similarly, the porous membrane 26 defines an infusion section 32 of catheter 20, and preferably covers the support 22 from the point 30 to the distal end of support 22. Alternatively, the catheter 20 may be configured without a non-porous membrane 24. In this configuration, the porous membrane 26 covers the entire length of the support 22, so that the entire length of the support 22 corresponds to the infusion section of the catheter 20. The infusion section can have any desired length. The proximal end of the catheter 20 may be connected to a fluid supply 34 containing a fluid 36 such as a liquid medication. The distal end of catheter 20 may include a cap 48 (FIG. 4) defining the endpoint of the axial lumens within the catheter 20.

In use, the catheter 20 is inserted into an anatomical system, such as a human body, to deliver fluid medication directly to a wound area within the anatomical system. In particular, the catheter 20 is designed to deliver medication throughout a generally linear segment of the wound area, corresponding to the infusion section 32 of the catheter 20. Thus, the catheter is preferably inserted so that the infusion section 32 is positioned within the wound area. By using well known methods, a physician or nurse may insert the catheter 20 with the aid of an axial guide wire 46 positioned within an axial guide wire lumen 44 of the catheter. Once the catheter is positioned as desired, the guide wire 46 is simply pulled back out through the proximal end of the catheter 20. Alternatively, the catheter 20 may be provided without a guide wire or a guide wire lumen.

FIGS. 2 and 3 illustrate a preferred configuration of the support 22. The surface of the support 22 includes interruptions such as a plurality of ribs 40 as shown in the figures. The interruptions are configured so that when the membranes 24 and 26 are wrapped around the support 22, the membranes form a portion of the walls of a plurality of axial lumens 38 within which the fluid 36 may flow. In a preferred configuration, a plurality of ribs 40 extend radially from a common axial center portion 42 of the support 22. The ribs 40 also extend longitudinally along a length of the support 22, and preferably along the entire length thereof. In the non-infusing section 28, shown in FIG. 2, the non-porous membrane 24 is preferably tightly wrapped around the outer edges of the ribs 40. As a result, the axial lumens 38 are formed between the inner surface of the non-porous membrane 24 and the outer surface of support 22. Similarly, in the infusion section 32, shown in FIG. 3, the porous membrane 26 is preferably tightly wrapped around the outer edges of the ribs 40, so that the axial lumens 38 are formed between the inner surface of porous membrane 26 and the outer surface of support 22.

In an alternative embodiment of the catheter 20, the porous membrane 26 may be wrapped around the entire length of the support 20, thus replacing the non-porous membrane 24. In this embodiment, the entire length of the support 22 corresponds to the infusion section 32. According to another alternative embodiment, the support 22 may extend only within the infusion section 32, and a tube may be provided extending from the fluid supply 34 to the proximal end of the support 22. In this embodiment, the tube replaces the non-porous membrane 24 and the portion of the support 22 extending within the non-infusing section 28 of the preferred embodiment. In other words, the tube defines the non-infusing section 28.

In the preferred configuration, the number of ribs 40 equals the number of axial lumens 38. Although five ribs 40 and axial lumens 38 are shown in FIGS. 2 and 3, any suitable number of ribs 40 and lumens 38 may be provided, giving due consideration to the goals of providing a plurality of lumens within the catheter 20, maintaining flexibility, and, if desired, maintaining the fluid independence of the lumens. Herein, the terms "fluid independence," "fluid separation," and the like, when used to describe a plurality of axial lumens, simply mean that the lumens do not fluidly communicate with each other. The membranes 24 and 26 are preferably glued along the outer edges of the ribs 40, utilizing any suitable glue, such as a medical grade glue or epoxy. This prevents the membranes 24 and 26 from slipping, which might occur as the catheter is inserted or removed from the anatomy. More preferably, the membranes are glued along the entire length of the outer edges of each of the ribs 40. Alternatively, the membrane may be wrapped around the support and not secured to the support by a foreign substance. The membrane and support may also be secured to each other by other means known to those of skill in the art. This maintains the fluid independence of the lumens 38. If desired, an axial guide wire lumen 44 may be provided within the axial central portion 42 of the support 22. The guide wire lumen 44 is adapted to receive a guide wire 46 which may be used to aid in the insertion of the catheter 20 into the anatomy, as described above and as will be easily understood by those of skill in the art.

As shown in FIG. 4, the catheter 20 preferably includes an end portion or cap 48 secured to the distal end of support 22. End portion 48 may be formed integrally with the support 22 or may be adhesively bonded thereto. Preferably, the proximal end of end portion 48 is circular and has a diameter such that the outer surface of the proximal end of end portion 48 is aligned with the outer edges of the ribs 40 of the support 22, as shown. The porous membrane 26 is wrapped around the proximal end of the end portion 48. The membrane 26 is preferably glued to the end portion 48 so that fluid 36 within the lumens 38 is prevented from exiting the catheter 20 without passing through the walls of the membrane 26. End portion 48 blocks axial fluid flow through the distal end of catheter 20. However, end portion 48 may optionally be formed from a porous material to permit some axial dispensation of fluid from the distal end of the catheter 20, if desired. The distal end of end portion 48 is preferably dome-shaped, as shown, to permit the catheter 20 to more easily be inserted into an anatomical region.

The support 22 can be formed from a variety of materials, giving due consideration to the goals of flexibility, lightweight, strength, smoothness, and non-reactivity to anatomical systems, i.e., safety. Suitable materials for the support 22 include nylon, polyamide, teflon, and other materials known to those skilled in the art. The porous membrane 26 is preferably a sponge-like or foam-like material or a hollow fiber. The membrane 26 may be formed from a variety of suitable materials, giving due consideration to the goals of being flexible and non-reactive to anatomical systems. The membrane 26 preferably has a porosity resulting in substantially uniform dispensation of fluid along the surface area of the infusion section 32 of the catheter 20, and has an average pore size sufficiently small to limit the flow of bacteria through the membrane walls. Some suitable materials for the membrane 26 are polyethylene, polysulfone, polyethersulfone, polypropylene, polyvinylidene difluoride, polycarbonate, nylon, high density polyethylene or any other hydrophilic material. These materials are advantageously biocompatible. The porous membrane 26 may filter out unwanted bacteria from the fluid medication as it passes through the membrane 26. It is known that the smallest bacteria cannot pass through a pore any smaller than 0.23 microns. Thus, the average pore size, or pore diameter, of the porous membrane 26 may be less than 0.23 microns to prevent bacteria from traversing the membrane 26. In other arrangements, however, the average pore size, or pore diameter, of the membrane 26 is preferably within the range of about 0.1 to 1.2 microns, more preferably within the range of about 0.3 to 1 micron, and even more preferably about 0.8 microns.

As mentioned above, the proximal end of catheter 20 may be connected to a fluid supply 34. The catheter 20 may be configured so that each axial lumen 38 is fluidly independent. In other words, the lumens 38 would not fluidly communicate with one another. The catheter 20 may be connected to a single fluid supply 34, so that the fluid 36 flows within each of the lumens 38. Alternatively, the catheter 20 may be connected to a plurality of separate fluid supplies so that several different fluids may separately flow within the lumens 38. According to this configuration, each lumen 38 may be connected to a separate fluid supply so that the total number of different fluids that may be delivered to the anatomy is equal to the number of lumens 38. Alternatively, the fluid lumens need not be fluidly independent. For example, the membrane 26 may not be secured to the support 22 along the entire length of the support 22, thus permitting fluid 36 to migrate between lumens 38.

In operation, the catheter 20 delivers fluid directly to the area of the anatomy that is adjacent to the infusion section 32. The fluid 36 from the fluid source 34 is introduced into the axial lumens 38 at the proximal end of the catheter 20. The fluid 36 initially flows through the non-infusing section 28. When the fluid 36 first reaches the infusion section 32, it soaks into the porous membrane 26. As more fluid 36 enters the infusion section 32, it diffuses longitudinally within the walls of the membrane 26 until the entire membrane 26 and infusion section 32 are saturated with fluid. At this point the fluid 36 begins to pass through the membrane 26, thereby exiting the catheter 20 and entering the anatomy. Moreover, the fluid 36 advantageously passes through the entire surface area of the porous membrane 26 at a substantially uniform rate, due to the characteristics of the membrane 26. Thus, the fluid is delivered at a substantially equal rate throughout a generally linear segment of the wound area of the anatomy. Furthermore, this advantage is obtained for both low and high pressure fluid delivery.

Figure 5:
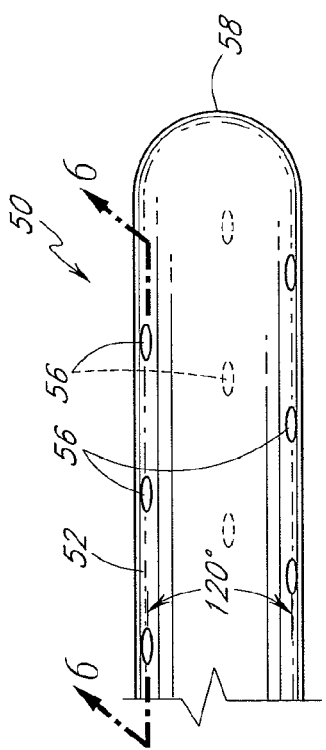
FIG. 5 is a side view of a catheter having features and advantages in accordance with a second embodiment of the present invention.
Figure 6:
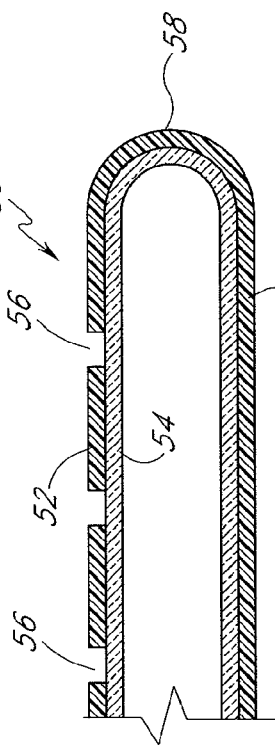
FIG. 6 is a cross-sectional view of the infusion section of the catheter of FIG. 5 taken along line 6-6 of FIG. 5.

FIGS. 5 and 6 illustrate a catheter 50 according to an alternative embodiment of the present invention. According to this embodiment, the catheter 50 includes an elongated outer tube 52 and an inner elongated tubular porous membrane 54. The tubular membrane 54 is preferably concentrically enclosed within the outer tube 52. More preferably, the tube 52 tightly surrounds and supports the tubular membrane 54 so that a relatively tight fit is achieved between the inner dimensions of tube 52 and the outer dimensions of membrane 54. A plurality of fluid exit holes 56 are provided within the tube 52, preferably throughout the entire circumference thereof. The portion of tube 52 that includes the exit holes 56 defines the infusion section of catheter 50. The tubular membrane 54 need only be provided along the length of the infusion section, but could be longer. Optionally, axial exit holes may be provided within the distal tip 58 of the tube 52. Also, a guide wire and/or guide wire lumen may be provided to aid in the insertion of the catheter 50 into the anatomy, as will be understood by those skilled in the art.

The tube 52 may be formed from any of a variety of suitable materials, such as nylon, polyether block polyamide, PTFE, polyimide, teflon and other materials known to those skilled in the art, giving due consideration to the goals of non-reactivity to anatomical systems, flexibility, light-weight, strength, smoothness, and safety. In a preferred configuration, the tube 52 is preferably a 19 to 20 gauge catheter tube, having inside and outside diameters of 0.021 inches and 0.035 to 0.043 inches, respectively. The exit holes 56 of tube 52 are preferably about 0.015 inches in diameter and provided at equally spaced axial positions along the tube 52. The holes 56 are preferably arranged so that every hole is angularly displaced about 120° relative to the longitudinal axis of the tube 52, from the angular location of the previous hole. The axial separation between adjacent exit holes 56 is preferably within the range of about 0.125 to 0.25 inches, and more preferably about 3/16 inch. Also, the infusion section can have any desirable length. This configuration results in a thorough, uniform delivery of fluid throughout a generally linear segment of the wound area. Of course, the exit holes 56 may be provided in any of a variety of alternative arrangements.

The tubular porous membrane 54 is preferably a sponge-like or foam-like material or a hollow fiber. The tubular membrane 54 may have an average pore size, or pore diameter, less than 0.23 microns to filter bacteria. In other arrangements, however, the pore diameter is preferably within the range of about 0.1 to 1.2 microns, more preferably within the range of about 0.3 to 1 micron, and even more preferably about 0.8 microns. The tubular membrane 54 may be formed from any of a variety of suitable materials, giving due consideration to the goals of non-reactivity to anatomical systems, maintaining flexibility, fitting within the size constraints of the tube 52, and having a porosity resulting in the substantially uniform dispensation of fluid through all of the exit holes 56 in tube 52. Some suitable materials for the membrane 54 are polyethylene, polysulfone, polyethersulfone, polypropylene, polyvinylidene difluoride, polycarbonate, nylon, high density polyethylene or any other hydrophilic material. Preferable inside and outside diameters of the tubular membrane 54 are 0.010 inches and 0.018 inches, respectively. In the event that a guide wire 46 is provided, the guide wire may be a stainless steel wire about 0.005 inches in diameter. The tube 52 may be secured to the membrane 54 by epoxy, cyanoacrylate or other means known to those skilled in the art. Alternatively, the membrane 54 may contact the tube 52 with an interference fit and not use other materials to secure the membrane 54 in the tube 52.

In operation, the catheter 50 delivers fluid to the region of an anatomical system adjacent to the infusion section of catheter 50. As the fluid flows into the infusion section, it initially soaks into the tubular porous membrane 54. As more fluid enters the infusion section, the fluid diffuses longitudinally within the walls of the tubular member 54. Once the membrane 54 and the tubular space therein are saturated, the fluid passes through the membrane 54 and exits the catheter 50 by flowing through the exit holes 56 of the tube 52. Moreover, the fluid advantageously passes through the membrane substantially uniformly throughout the surface area of the membrane 54, resulting in a substantially uniform flow through substantially all of the exit holes 56. Thus, the fluid is delivered at a substantially equal rate throughout the wound area of the anatomy. Furthermore, this advantage is obtained for both low and high pressure fluid delivery.

Figure 7:
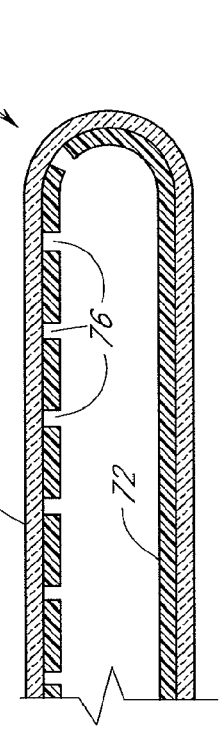
FIG. 7 is a cross-sectional view of a catheter having features and advantages in accordance with a third embodiment of the present invention.

FIG. 7 illustrates a catheter 70 according to another embodiment of the present invention. Catheter 70 includes a tube 72 having a plurality of exit holes 76 in side walls of the tube, and a tubular porous membrane 74 concentrically enclosing the tube 72. Catheter 70 operates in a similar manner to catheter 50 described above in connection with FIGS. 5 and 6. In use, fluid medication passes through the exit holes 76 and then begins to soak into the porous membrane 74. The fluid diffuses longitudinally within the walls of the membrane until the membrane is saturated. Thereafter, the fluid leaves the membrane walls and enters the anatomy. Advantageously, the fluid is dispensed to the anatomy at a substantially uniform rate throughout the surface area of the membrane 74. As in the previous embodiments, this advantage is obtained for both low and high pressure fluid delivery.

FIG. 8 illustrates a catheter 60 according to another embodiment of the present invention. Catheter 60 is better suited for relatively high flow rate delivery of fluid to a region within an anatomical system. Catheter 60 includes a tube 62 having a plurality of exit holes 64 of increasing size. In particular, the more distal exit holes are larger in diameter than the more proximal exit holes. The position of the exit holes 64 on the tube 62 defines the length of the infusion section of the catheter 60. The infusion section can have any desired length. The proximal end of catheter 60 is connected to a fluid supply, and a guide wire and/or guide wire lumen may also be provided for aiding in the insertion of catheter 60 into the anatomy.

As discussed above, for high or low pressure fluid delivery, exit holes nearer to the distal end of a catheter tube generally have increased flow resistance compared to exit holes nearer to the proximal end of the tube. Also, the fluid flowing through the more distal holes experiences a greater pressure drop. Consequently, there is generally a greater flow rate of fluid through the more proximal holes, resulting in non-uniform fluid delivery. In contrast, catheter 60 advantageously provides substantially uniform fluid delivery through substantially all of the exit holes 64, under relatively high flow rate conditions. This is because the larger size of the more distal holes compensates for their increased flow resistance and pressure drop. In other words, since the more distal holes are larger than the more proximal holes, there is a greater flow rate through the more distal holes than there would be if they were the same size as the more proximal holes. Advantageously, the holes 64 are provided in a gradually increasing size which results in substantially uniform fluid delivery. In addition, the exit holes 64 may be sized so that they combine to form a flow-restricting orifice, as described below in connection with the embodiment of FIG. 12.

As compared to prior art catheters, catheter 60 is advantageously simple and easy to manufacture. All that is required is to drill a plurality of exit holes 64 in the tube 62. Furthermore, catheter 60 can sustain greater bending than prior art catheters while maintaining operability. In contrast to prior art catheters, such as the Wang catheter, if the tube 62 is bent somewhat, it will still deliver fluid relatively uniformly. This is because the tube 62 has a single lumen with a relatively large cross-section. When the tube 62 is somewhat bent, fluid flowing within the lumen is less likely to experience blockage and a consequent pressure change which might lead to non-uniform fluid dispensation.

The tube 62 of catheter 60 may be formed from any of a wide variety of materials, giving due consideration to the goals of non-reactivity to anatomical systems, flexibility, light-weight, strength, smoothness, and safety. Suitable materials include nylon, polyether block polyamide, PTFE, polyimide, teflon, and other materials known to those skilled in the art. The infusion section can have any desired length but is preferably about 0.5 to 20 inches long, and more preferably about 10 inches long. The diameter of the exit holes 64 preferably ranges from about 0.0002 inches at the proximal end of the infusion section to about 0.01 inches at the distal end thereof. The largest, i.e., most distal, exit hole 64 is preferably about 0.25 inches from the distal end of the tube 62. In the preferred configuration, the axial separation between adjacent holes 64 is within the range of about 0.125 to 0.25 inches, and more preferably about 3/16 inch. Optionally, the holes 64 may be provided so that adjacent holes are angularly displaced by about 120 degrees as in the embodiment of FIG. 5. Of course, if too many exit holes 64 are provided, the tube 62 may be undesirably weakened.

Figure 9:
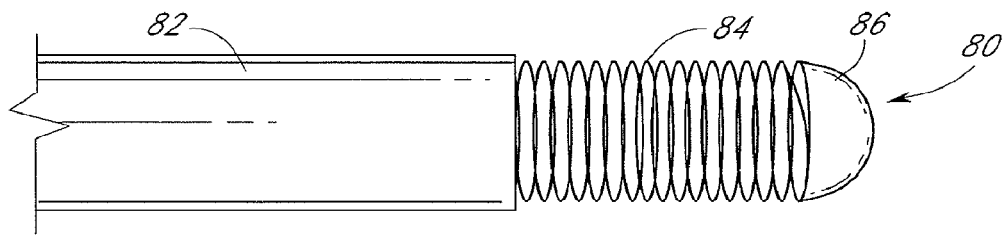
FIG. 9 is a side view of a catheter having features and advantages in accordance with a fifth embodiment of the present invention.
Figure 10A:
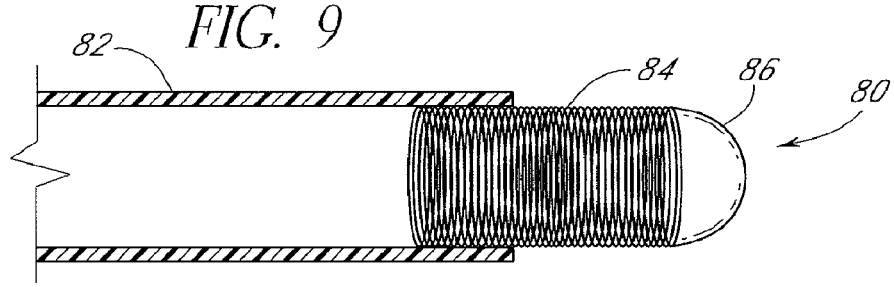
FIG. 10A is a cross-sectional view of the catheter of FIG. 9, illustrating an unstretched state of the spring.
Figure 10B:
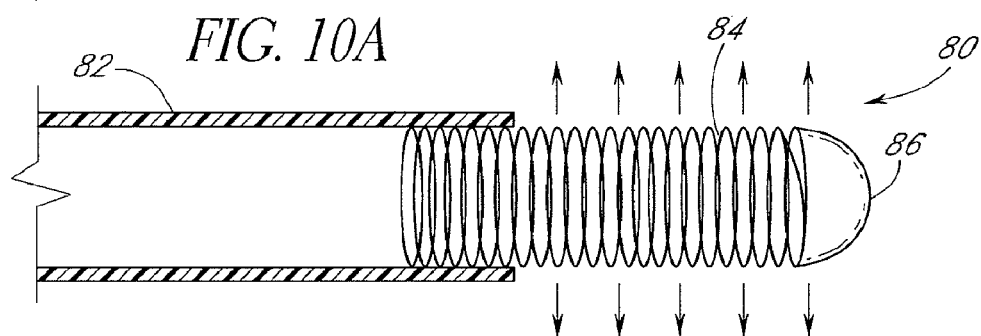
FIG. 10B is a cross-sectional view of the catheter of FIG. 9, illustrating a stretched state of the spring.

FIGS. 9, 10A, and 10B illustrate a catheter 80 according to another embodiment of the present invention. The catheter 80 comprises a tube 82, a "weeping" tubular coil spring 84, and a stop 86. The proximal end of the spring 84 is attached to the distal end of the tube 82 so that the tube and spring each define a portion of a central lumen. A preferably dome-shaped stop 86 is attached to and closes the distal end of the spring 84. The portion of the spring 84 that is distal to the tube 82 comprises the infusion section of the catheter 80. In an unstretched state, shown in FIG. 10A, the spring 84 has adjacent coils in contact with one another so that fluid within the spring and below a threshold dispensation pressure is prevented from exiting the lumen by flowing radially between the coils. The spring 84 has the property of stretching longitudinally, as shown in FIG. 10B, when the fluid pressure is greater than or equal to the threshold dispensation pressure of the spring, thereby permitting the fluid to be dispensed from the lumen by "weeping," i.e., leaking radially outward between the coils. Alternatively, the spring may stretch radially without elongating to permit fluid to weep through the coils of the spring. Further, the spring may stretch both longitudinally and radially to permit weeping, as will be understood by those of skill in the art. Advantageously, the fluid between the coils of the spring is dispensed substantially uniformly throughout the length and circumference of the portion of the spring that is distal to the tube 82, i.e., the infusion section. The catheter 80 can be used for both high or low flow rate fluid delivery.

In use, the catheter 80 is inserted into an anatomical region so that the spring 84 is in a region to which fluid medication is desired to be delivered. The spring is initially in an unstretched state, as shown in FIG. 10A. The fluid is introduced into a proximal end of the tube 82 of the catheter 80 and flows into and through the spring 84 until it reaches the stop 86. As fluid is continually introduced into the proximal end of the tube 82, the fluid builds inside of the spring 84. When the spring 84 is filled with fluid, the fluid pressure rises more quickly. The fluid imparts a force directed radially outward onto the spring coils. As the pressure builds, the outward force becomes larger. Once the fluid pressure rises to the threshold dispensation pressure, the outward force causes the spring coils to separate slightly so that the spring stretches longitudinally, as shown in FIG. 10B. Alternatively, the coils may separate radially, as discussed above. The fluid then flows through the separated coils to be dispensed from the catheter 80. Moreover, the dispensation is advantageously uniform throughout the infusion section of the catheter 80. As fluid is continually introduced into the tube 82, the spring 84 remains stretched to continually dispense fluid to the desired region within the anatomy. If the fluid introduction temporarily ceases, the fluid pressure within the spring 84 may fall below the threshold dispensation pressure. If so, the spring will compress so that the coils are once again adjacent and the fluid is no longer dispensed.

Several spring types will achieve the purposes of this invention. Suitable stainless steel spring types are 304, 316L or 402L, which can be readily purchased. In a preferred configuration, the spring 84 has about 200 coils per inch along its length. In this configuration, the spring can advantageously sustain a high degree of bending without leaking fluid from within, and only a severe bend will cause adjacent coils to separate. Thus, the spring 84 may be flexed considerably within an anatomical region without causing fluid to leak and therefore be dispensed to only one region within the anatomy. The spring 84 can have any desired length to define the length of the infusion section of the catheter 80. The spring may be formed from a variety of materials, giving due consideration to the goals of strength, flexibility, and safety. A preferred material is stainless steel. In the preferred configuration, the inside and outside diameters of the spring are about 0.02 inches and 0.03 inches, respectively, and the spring wire has a diameter of about 0.005 inches. The proximal end of the spring 84 is preferably concentrically enclosed within the distal end of the tube 82. The spring can be glued to the inside wall of the tube 82 using, for example, a U.V. adhesive, a potting material, or other bonding materials. Alternatively, the spring can be soldered within the tube 82 or be fitted with a proximal plug and tightly plugged into the tube 82.

The tube 82 and stop 86 can be formed from any of a variety of materials, giving due consideration to the goals of flexibility, light-weight, strength, smoothness, and safety. Suitable materials include nylon, polyether block polyamide, PTFE, polyimide, teflon, and other materials known to those skilled in the art.

Figure 11:
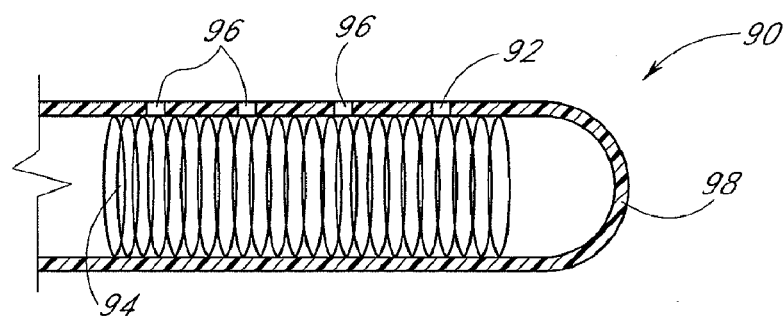
FIG. 11 is a cross-sectional view of a catheter having features and advantages in accordance with a sixth embodiment of the present invention.

FIG. 11 illustrates a catheter 90 according to another embodiment of the present invention. The catheter 90 comprises a distally closed tube 92 and a "weeping" tubular coil spring 94 concentrically enclosed within the tube 92 so that a lumen is defined within the tube and spring. A plurality of exit holes 96 are provided along a length of the tube 92, in the side wall thereof. The length of the tube 92 including such exit holes 96 defines an infusion section of the catheter 90. The exit holes 96 are preferably provided throughout the walls of the infusion section. The infusion section can have any desired length. In the preferred configuration, the axial spacing between adjacent holes 96 is within the range of about 0.125 to 0.25 inches, and more preferably about 3/16 inch. Adjacent holes 96 are preferably angularly spaced apart by about 120 degrees. The spring 94 is preferably enclosed within the infusion section of the catheter and configured similarly to the spring 84 of the embodiment of FIGS. 9, 10A and 10B. The spring 94 is preferably longer than the infusion portion and positioned so that all of the exit holes 96 are adjacent to the spring 94. In this configuration, the fluid is prevented from exiting the lumen without flowing between the spring coils. A stop is preferably attached to the tube to close the distal end thereof. Alternatively, the tube 92 may be formed with a closed distal end. The catheter 90 can be used for high or low flow rate fluid delivery.

In use, the catheter 90 is inserted into an anatomical region so that the infusion section is in a region to which fluid medication is desired to be delivered. The fluid is introduced into a proximal end of the tube 92 of the catheter 90 and flows through the spring 94 until it reaches the closed distal end of the tube 92. As fluid is continually introduced into the proximal end of the tube 92, the fluid builds inside of the spring 94. Eventually, the spring 94 becomes filled with fluid, the fluid pressure rises, and the fluid weeps through the spring coils as described above in connection with the embodiment of FIGS. 9, 10A, and 10B. Moreover, the fluid flows through the spring coils substantially uniformly throughout the length and circumference of the spring 94. The fluid then exits the tube 92 by flowing through the exit holes 96 of the infusion section. The exit holes are preferably equal in size so that the fluid flows at a substantially equal rate through the exit holes, advantageously resulting in a generally uniform distribution of fluid throughout a desired region of the anatomy. As fluid is continually introduced into the catheter 90, the spring 94 remains stretched to continually dispense fluid from the catheter. If the fluid introduction ceases temporarily, the fluid pressure within the spring 94 may fall below the threshold dispensation pressure. If so, the spring may compress so that the coils are once again adjacent and the fluid is no longer dispensed.

In the preferred configuration, the spring 94 and tube 92 are in contact along the entire length of the spring, so that the fluid weeping through the spring is forced to flow through the holes 96 of the infusion section. Preferably, one end of the spring 94 is attached to the inside walls of the tube 92, permitting the other end of the spring to be displaced as the spring stretches. The spring can be glued to the tube 92 with, for example, a U.V. adhesive, potting material, or other bonding materials. Alternatively, an end of the spring can be soldered onto the inner walls of the tube 92. The tube 92 can be formed from any suitable material. The inside walls of the tube 92 are preferably smooth so that the spring can more freely stretch and compress.

Figure 12:
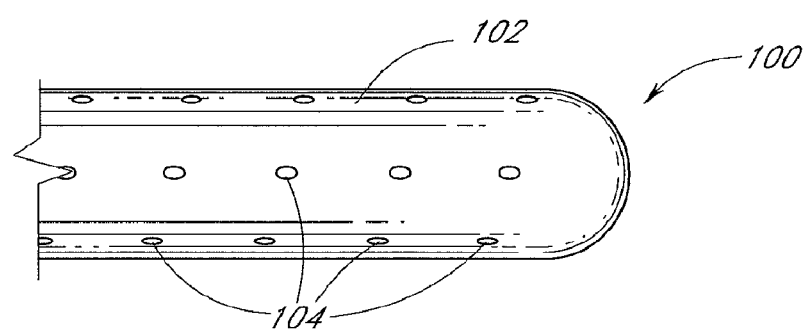
FIG. 12 is a side view of a catheter having features and advantages in accordance with a seventh embodiment of the present invention.

FIG. 12 illustrates a catheter 100 according to another embodiment of the present invention. The catheter 100 comprises a distally closed tube 102 having a plurality of exit holes 104 in side walls of the tube 102. The portion of the tube 102 having exit holes 104 defines an infusion section of the catheter 100. The exit holes 104 are sized to have a combined area of opening that is smaller than the area of any other flow-restricting cross-section or orifice of the catheter. Thus, the exit holes 104 are the flow-restrictor of the catheter 100. In use, the catheter advantageously dispenses fluid through substantially all of the exit holes 104. A fluid introduced into a proximal end of the tube 102 flows through the tube until it reaches the closed distal end thereof. At this point, the fluid builds within the infusion portion of the catheter. The fluid is substantially prevented from flowing through the holes 104, due to their small size. Eventually, the infusion portion of the catheter becomes filled with fluid. As fluid is continually introduced into the proximal end of the tube 102, the fluid pressure begins to build. At some point the pressure becomes sufficiently high to force the fluid through the exit holes 104. Moreover, the fluid flows through substantially all of the exit holes 104.

In this preferred configuration, the exit holes 104 are all equal in size so that the fluid is dispensed at a substantially equal rate through substantially all of the holes. The holes 104 are preferably laser drilled to achieve a very small hole diameter. A preferred diameter of the exit holes 104 is about 0.0002 inches, or about 5 microns. Numerous exit holes 104 may be provided within the tube 102. The holes are advantageously provided throughout the circumference of the infusion portion of the catheter 100, to more uniformly deliver the fluid throughout an anatomical region. A preferred axial spacing between adjacent holes 104 is within the range of about 0.125 to 0.25 inches, and more preferably about 3/16 inch. The catheter 100 can be used for high or low flow rate fluid delivery. The tube 102 can be formed from any of a variety of materials known to those skilled in the art and discussed previously.

Figure 13:
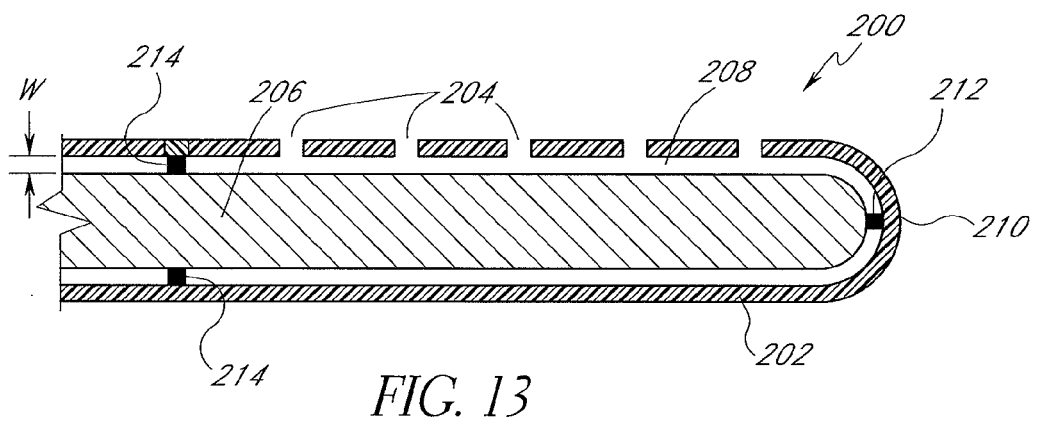
FIG. 13 is a longitudinal cross-sectional view of a catheter having features and advantages in accordance with an eighth embodiment of the present invention.

FIG. 13 illustrates a catheter 200 according to another embodiment of the present invention. Catheter 200 includes a distally closed tube 202 having a plurality of exit holes 204 therein along an infusion section of the catheter, as in the above-described embodiments. The holes 204 are desirably provided throughout the circumference of the tube 202. Enclosed within the tube 202 is an elongated member 206 formed of a porous material. Preferably, the member 206 is generally cylindrical in shape, and solid. Preferably, the member 206 is positioned within the tube 204 so that an annular space 208 is formed between the outer surface of the member 206 and the inner surface of the tube 202. Preferably, the member 206 extends from the distal end 210 of the tube 202 rearwardly to a point proximal of the infusion section of the catheter. Alternatively, the member 206 may extend along only a portion of the infusion section. The member 206 is preferably generally concentric with the tube 202, but non-concentric designs will achieve the advantages of the invention. Preferably, the member 206 is manufactured of a flexible material to assist with the placement of the catheter 200 in the body of a patient.

In operation, fluid medication flowing in the tube 202 saturates the porous member 206 and flows into the annular region 208. Once the member 206 is saturated, the fluid in the member 206 flows into the region 208 and out of the catheter 200 through the exit holes 204. Advantageously, since the fluid pressure is uniform throughout the annular region 208, the fluid flows substantially uniformly through all of the holes 204. There are several advantages of the annular region 208. One advantage is that it tends to optimize the uniformity of flow through the exit holes 204. Also, the member 206 may be formed from a porous material that tends to expand when saturated with liquid. If so, the member 206 preferably expands into the annular region 208 without pressing against the tube 202. This limits the possibility of high pressure regions at the interior surface of the tube 202, which could cause uneven exit flow of the medication within the wound site. Alternatively, the member 206 may expand and come into contact with the tube 202, and still accomplish the goals of the present invention.

The member 206 is formed of a porous material having an average pore size preferably within the range of 0.1-50 microns, and more preferably about 0.45 microns. The radial width W of the annular region 208 is preferably within the range of 0 to about 0.005 microns, and more preferably about 0.003 microns. The member 206 can be formed of any of a variety of materials, giving due consideration to the goals of porosity, flexibility, strength, and durability. A preferred material is Mentek.

Figure 14:
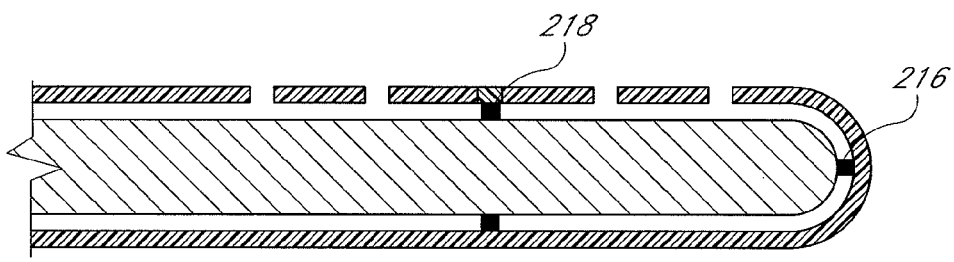
FIG. 14 is a longitudinal cross-sectional view of a catheter similar to that of FIG. 13, illustrating a first attachment alternative between the internal porous member and the tube.
Figure 15:
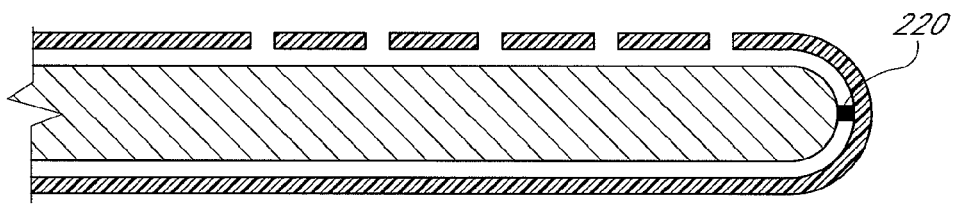
FIG. 15 is a longitudinal cross-sectional view of a catheter similar to that of FIG. 13, illustrating a second attachment alternative between the internal porous member and the tube.
Figure 16:
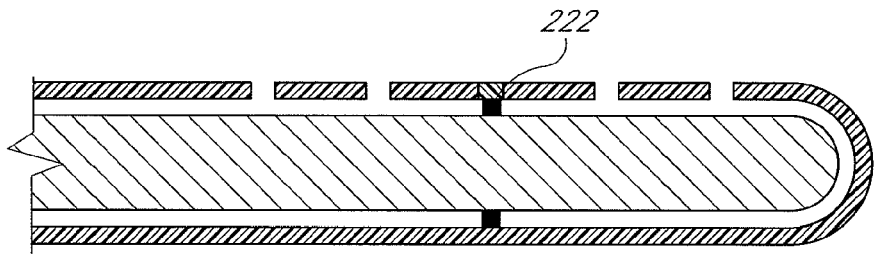
FIG. 16 is a longitudinal cross-sectional view of a catheter similar to that of FIG. 13, illustrating a third attachment alternative between the internal porous member and the tube.

The member 206 can be secured within the tube 202 by the use of an adhesive. In one embodiment, as shown in FIG. 13, the adhesive is applied at the distal end of the member 206 to form a bond with the interior surface of the distal end of the tube 202. Preferably, adhesive is applied at or near the proximal end of the infusion section of the catheter 200. Additionally, the adhesive can be applied to the circumference of the member 206 at any longitudinal position thereof, forming a ring-shaped bond with the interior surface of the tube 202. For example, in the embodiment of FIG. 13, a ring-shaped bond 214 is provided just proximal of the infusion section of the catheter 200. Other configurations are possible. For example, FIG. 14 shows an embodiment in which the adhesive is applied to the distal end of the member 206 to form a bond 216, and also at generally the center of the infusion section to form a ring-shaped bond 218. FIG. 15 shows an embodiment in which the adhesive is applied only to the distal end of the member 206 to form a bond 220. FIG. 16 shows an embodiment in which the adhesive is applied only to the center of the infusion section to form a ring-shaped bond 222. Those of ordinary skill in the art will understand from the teachings herein that the adhesive may be applied in any of a variety of configurations. Thus, for example, adhesive at the distal end of the catheter (i.e., 212, 216, and 220 in FIGS. 13, 14, and 15, respectively) is not required.

In a presently preferred embodiment of the invention, preferably one bond is incorporated at the most proximal hole of the catheter. The bond preferably is formed with an adhesive as described below.

The ring-shaped bond 214 can be formed by pouring the adhesive in liquid form through one of the exit holes 204 when the member 206 is in the tube 202. The adhesive, having a generally high viscosity, tends to flow about the circumference of the member 206, rather than into the body of the member. The adhesive thus forms a ring-shaped bond with the tube 202, as will be understood by those of skill in the art. Also, the adhesive plugs the exit hole 204 through which it is poured. Any of a variety of different types of adhesives will be acceptable, a preferred adhesive being Loctite.

Figure 17:
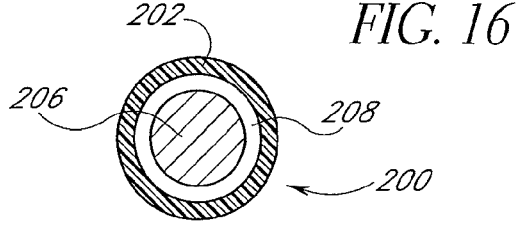
FIG. 17 is a transverse cross-sectional view of a catheter according to FIGS. 13-16, wherein the internal porous member is concentric with the outer tube.
Figure 18:
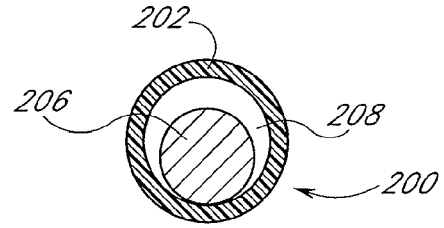
FIG. 18 is a transverse cross-sectional view of a catheter according to FIGS. 13-16, wherein the internal porous member is not concentric with the outer tube.

As mentioned above, the member 206 is preferably concentric with the tube 202. FIG. 17 shows a cross-section of a catheter 200 in which the member 206 is concentrically enclosed within the tube 202. Alternatively, the member 206 may be positioned adjacent to the tube 202, as shown in FIG. 18. The configuration of FIG. 18 may be easier to manufacture than that of FIG. 17, since the member 206 does not have to be centered within the tube 202.

Those of ordinary skill in the art will understand from the teachings herein that the member 206 can be of any desired length and can extend along any desired length of the infusion section of the catheter 200. For example, the member 206 does not have to extend to the distal end of the tube 202. Further, the proximal end of the member 206 may be either distal or proximal to the proximal end of the infusion section.

Figure 19:
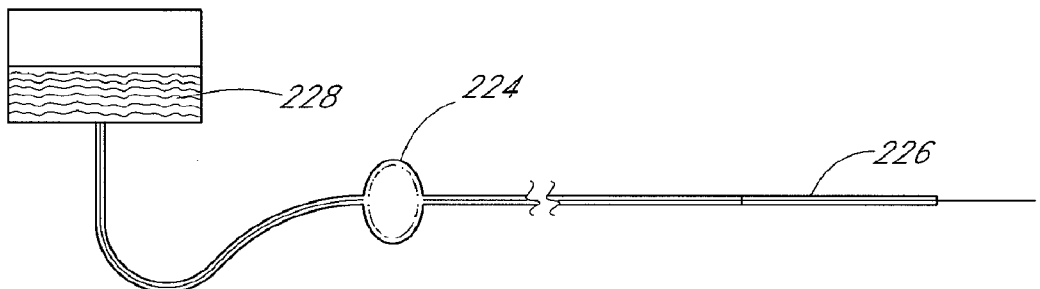
FIG. 19 is a schematic illustration of a catheter of the present invention used in conjunction with an air eliminating filter.

When any of the catheters of the above embodiments is used, the catheter may initially have air inside of the catheter tube. For example, the catheter 200 shown in FIG. 13 may have air inside of the porous material of the member 206. The introduction of liquid medication into the catheter forces the air to flow out of the exit holes. However, this may take several hours. If the catheter is inserted into a patient while air is inside, and liquid medication is introduced into the catheter, the patient's wound site may receive little or no medication until air is expelled from the catheter tube. Thus, it is preferred to run the liquid medication through the catheter prior to inserting the catheter into a patient, to ensure that the air is expelled from the catheter prior to use. Further, with reference to FIG. 19, an air filter 224, as known in the art, can be inserted into the catheter tubing proximal the infusion section 226 of the catheter 200. The filter 224 prevents undesirable air from entering the infusion section 226 of the catheter 200.

Figure 20:
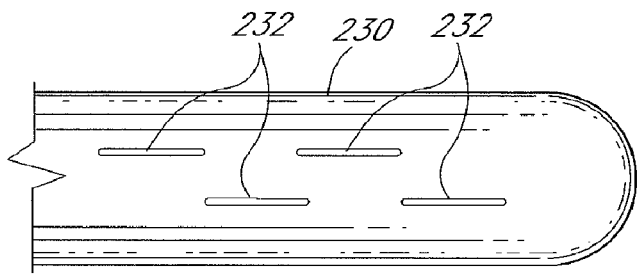
FIG. 20 is a side view of a catheter having features and advantages in accordance with a ninth embodiment of the present invention.
Figure 21:
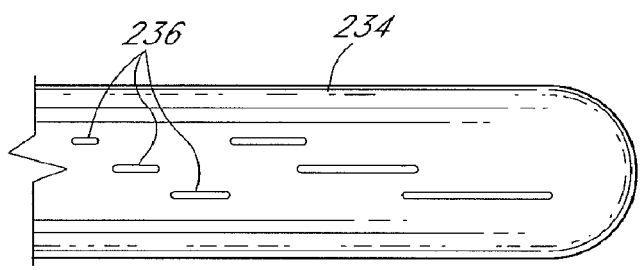
FIG. 21 is a side view of a catheter having features and advantages in accordance with a tenth embodiment of the present invention.

FIGS. 20 and 21 illustrate catheter tubes having elongated exit holes or slots. These catheter tubes may be used in place of the catheter tubes shown and described above. FIG. 20 shows a tube 230 having exit holes or slots 232 that are elongated in the longitudinal direction of the tube 230. The slots 232 are preferably provided throughout the circumference of the tube 230, along the infusion section of the catheter. Compared to smaller exit holes, the elongated slots 232 tend to increase the flowrate of fluid exiting the catheter, by reducing the flow impedance experienced by the fluid. Preferably, the slots 232 may be oriented longitudinally on the catheter body so as not to compromise the structural integrity of the catheter 200, as will be easily understood by those of skill in the art.

FIG. 21 shows a tube 234 having exit holes or slots 236 whose lengths increase along the length of the tube in the distal direction. In the illustrated embodiment, the slots nearer to the proximal end of the infusion section of the tube 234 are shorter in length than the slots nearer to the distal end of the infusion section. As in the embodiment of FIG. 8, the catheter tube 234 advantageously provides substantially uniform fluid delivery through substantially all of the exit slots 236, under relatively high flow rate conditions. This is because the larger size of the more distal slots compensates for their increased flow resistance and pressure drop. In other words, since the more distal slots are larger than the more proximal slots, there is a greater flow rate through the more distal slots than there would be if they were the same size as the more proximal slots. Advantageously, the slots 236 are provided in a gradually increasing length, which results in substantially uniform fluid delivery. Further, the elongated slots result in generally higher exit flowrates, as in the embodiment of FIG. 20.

With regard to all of the above embodiments of catheters, an independent guide wire lumen may be provided within or adjacent to the lumen(s) disclosed, as will be understood by those skilled in the art.

Figure 22:
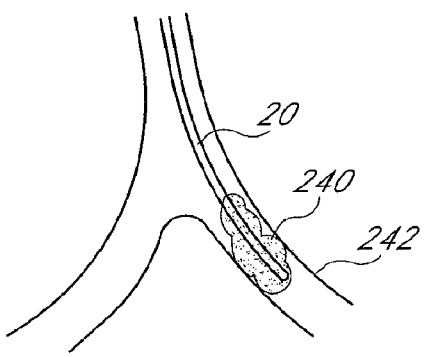
FIG. 22 is a schematic illustration of the use of a catheter of the present invention for treating a blood clot.

The catheters of the present invention can be used in various medical applications. With reference to FIG. 22, in one exemplary application a catheter 20 (reference numeral 20 is used to identify the catheter, but any of the above-described catheters can be used) is inserted into a blood clot 240 inside of a vein or artery 242. Preferably, the infusion section of the catheter is within the blood clot 240. Liquid medication is preferably introduced into the proximal end of the catheter tube. Advantageously, the medication exits the catheter 20 at a uniform rate throughout the infusion section to dissolve the clot 240.

As will be easily understood by those of skill in the art, any of the catheter embodiments described herein may be used in a variety of applications including, but not limited to, peripheral nerve blocks, intrathecal infusions, epidermal infusions, intravascular infusions, intraarterial infusions and intraarticular infusions, as well as in wound site pain management. Furthermore, the disclosed catheters may be adapted for use as aspiration catheters, as well.

In addition, any of the catheters disclosed herein may be integral with a fluid line emanating from an infusion pump as opposed to being an independent catheter designed to be connected or secured to an infusion pump.

FIGS. 23-32 illustrate several preferred embodiments of a catheter having features configured to facilitate the uniform flow of a fluid exiting the catheter. These flow control features preferably are similar to the features described above with reference to FIGS. 1-21. Furthermore, the catheters of FIGS. 23-32 may be constructed of similar materials using processes similar to those described above, unless otherwise noted. In addition, preferably the catheters of FIGS. 23-32 also include anti-microbial properties to inhibit the growth of microbes on or within the catheter and, preferably, to inhibit microbe growth in an anatomical region adjacent the catheter. As described in greater detail below, the illustrated catheters may include an anti-microbial layer, anti-microbial materials embedded within the material from which components of the catheters are constructed, or a combination of anti-microbial layers and embedded anti-microbial materials.

In preferred arrangements, the anti-microbial layers or materials are configured to provide the sustained release of anti-microbial agents. In one arrangement, the anti-microbial layer or material comprises a heavy metal such as gold, platinum, silver, zinc or copper, all of which are known to possess anti-microbial properties and, more preferably, the heavy metal is in the form of metal ions. In a particularly preferred embodiment, the anti-microbial layer or material is silver and, more preferably, silver ions. However, other anti-microbial substances such as antibiotics or germicidal chemicals may also be used or incorporated on or in the catheter.

In some arrangements, the metal ions may be contained within a carrier material, such as a natural or synthetic polymer, which preferably assists in the sustained release of the metal ions and inhibits degradation of the metal ions. Other suitable methods for providing for the sustained release of the anti-microbial substances may also be used.

As described above, in certain arrangements, the anti-microbial material may be in the form of a layer of material making up a portion of a component of the catheter, such as the tubular catheter body or a flow control component, for example. To create such an anti-microbial layer, the anti-microbial material may be applied as a coating to a component of the catheter, such as by a deposition, dipping, spraying, co-extrusion, or other techniques or processes suitable for creating a multi-layered article.

In alternative arrangements, the anti-microbial material may be dispersed within the base material(s) that construct a component of the catheter, such that the base material forms an anti-microbial layer. For example, the anti-microbial material may be compounded or otherwise embedded or dispersed within the polymer material forming the catheter body. However, the anti-microbial material may be embedded within other components of the catheter, as described in greater detail below. The anti-microbial material may be provided within the base material prior to the process of manufacturing the catheter component. For example, the anti-microbial material may be provided within the polymer resin used to create the catheter body by extrusion or other forming processes.

Preferably, the anti-microbial substance is both embedded within a base material of the catheter tube or other catheter components and forms a layer on the tube or other component(s). In one particularly preferred arrangement, the anti-microbial substance comprises stabilized ionic silver nanoparticles, which preferably are less than about 50 nm in size and, more preferably, are between about 5 to 15 nm in size, in a solution.

The catheter (or catheter component) is preferably submerged into the solution, which in one arrangement may comprise silver chloride with a reducing agent. The catheter preferably is submerged in the solution for a period of time sufficient to permit the silver particles to adhere to the catheter. In one arrangement, the catheter is submerged for about 16 hours in a solution that is above room temperature. For example, the temperature of the solution may be approximately 35 degrees Celsius. Desirably, multiple catheters are submerged in a container of solution at the same time. Preferably, the solution and/or catheters are agitated to assist in providing a uniform silver particle distribution throughout the length of the catheters and, desirably, on both inner and outer surfaces of the catheters. In one preferred method, the catheter body (or tubular portion of the catheter assembly) is treated with the anti-microbial substance separate from the flow control components, such as those described above. If desired, the flow control components, such as the hollow fiber member or membrane, may be treated with the anti-microbial substance separately. The catheter body and flow control component(s) may then be assembled.

Once the catheters have been submerged in the silver solution for a desirable period of time, the catheters are removed from the solution and, preferably, rinsed. The rinsing agent is alcohol in one preferred method of manufacture. After rinsing, the catheters are allowed to dry. If desired, means may be provided to assist the drying of the catheters. For example, the catheters may be spun. In one arrangement, the catheters are spun at approximately 80-100 rpm for about two minutes. After spinning, the catheters preferably are allowed to fully dry, preferably overnight.

The dried catheters preferably are then exposed to light. Catheters which have been submerged in silver solutions and are then exposed to light change in color or become colored. For example, typical nylon catheters usually are clear or opaque and become colored after submersion in the silver particle solution. Catheters exposed to certain silver solutions, such as those disclosed herein, may take on a gold or amber coloration. The coloration of such catheters enhances the ease of identification of treated catheters in contrast to untreated catheters. It is believed that the silver treated catheters described herein are the only non-clear, or colored, catheters used for wound site, peripheral nerve block or epidural applications and, thus, the coloration will provide the advantage of easy identification that the catheters possess anti-microbial properties.

During the submersion of the catheters, the nanoparticles are able to become lodged in surface imperfections in the catheter tube, or other components, such as the flow control membrane (hollow fiber), for example. Furthermore, due to their small size and charge, the silver nanoparticles tend to stick to the surface of the catheter tube or other component that is being treated. Thus, in this preferred arrangement, the anti-microbial substance is both impregnated and coated onto the catheter. The catheters are then dried. The silver ions are then released over time when the catheter comes into contact with moisture, such as when placed within a body.

The silver nanoparticles may be created by any suitable process. In one preferred arrangement, the silver nanoparticles are prepared by adding a reducing agent to silver chloride. Such compositions are well-suited for use in the commercial scale manufacture of medical devices, such as the catheters disclosed herein. However, other suitable methods of producing silver nanoparticles may also be used. In a preferred arrangement, the catheter body is constructed from a nylon material and the anti-microbial material is applied to and/or impregnated within the nylon.

Preferably, the anti-microbial substance is configured for sustained release by the catheter. In a fluid delivery catheter, the anti-microbial substance may be released into the fluid, and carried by the fluid into the anatomical region adjacent the catheter. Such an arrangement advantageously inhibits microbe growth both in the catheter and in the region adjacent the catheter, as the anti-microbial substances are likely to travel a greater distance within the anatomical region with the fluid being dispensed than when only released to the tissue from the catheter body itself. Accordingly, it is preferred that the catheter is configured to release anti-microbial substances into the fluid being dispensed, such as by treating the internal (lumen-defining) surface of the catheter or the above-described flow control components. In the case of a wound site pain management application, advantageously, such a catheter would not only provide pain management substances, but would also inhibit microbe growth, and infection, in the wound site.

Preferably, the catheter is configured to release an anti-microbial substance at an elution rate of between about 0.8 and 3.0 µg/cm for at least the infusion section of the catheter and, preferably, for at least the entire portion of the catheter internal to the patient. Preferably, the catheter is configured to maintain such an anti-microbial release over an expected duration of use of the catheter. In one arrangement, the catheter is configured to maintain a significant release of an anti-microbial substance for a minimum of 10 days.

In addition, in some preferred arrangements, the catheter is configured to release a greater amount of an anti-microbial substance initially (a bolus dose) and then maintain a lesser dose thereafter. For example, in one preferred arrangement, the catheter releases a greater amount of an anti-microbial substance for the first 5 days after placement and then maintains a substantially constant lower level of release for at least about 5 days thereafter. However, in other arrangements, release of the anti-microbial substance may be relatively constant or may decline over time in a generally linear fashion. For a 20 gauge catheter, preferably, about 15% of the silver particle content is released within about 10 days. In other applications, however, a lesser or greater release of anti-microbial substances or agents may be desired.

Preferably, the catheter is treated to contain, or is loaded with, a sufficient amount of the anti-microbial substance to obtain desirable elution rates. The anti-microbial content of the catheter may be varied by altering the time of submersion in the anti-microbial substance solution, for example. In a 20 gauge catheter containing silver nanoparticles, it is preferred that the catheter be loaded to a level such that the ratio of silver particles to the base material of the catheter (or treated catheter component) is about 600-2000 parts per million (ppm). In one preferred arrangement, the catheter is loaded to a level of about 1000 ppm. Such silver nanoparticle contents were determined to produce satisfactory elution rates which encompassed the above-recited ranges. For example, a catheter containing approximately 600 ppm, the elution rate was found to average approximately 1.8 µg/cm for the first 5 days and approximately 0.8 µg/cm for the next 5 days. A catheter containing approximately 1000 ppm provided an elution rate of about 3.0 µg/cm for the first 5 days and about 1.4 µg/cm for the next 5 days. In addition, the silver nanoparticle contents of the catheter may be modified to produce other desired elution rates.

Figure 23:
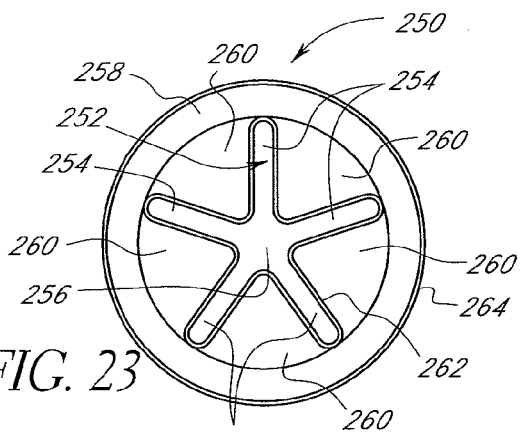
FIG. 23 is a cross-sectional view of a catheter similar to the catheter of FIGS. 1-4 and having an anti-microbial layer on the membrane and support.

FIG. 23 is a cross-sectional view of an anti-microbial catheter 250, which preferably is configured to provide substantially uniform fluid flow over the infusion section of the catheter 250, similar to the catheter 20 described above with respect to FIGS. 1-4. However, in some arrangements, the catheter 250 (or other catheters disclosed herein) may be configured as aspiration catheters to remove fluid from a site. The catheter 250 of FIG. 23 includes an internal support member 252. The support 252 preferably includes a plurality of ribs 254 extending radially outward from an elongate base portion 256. Preferably, the ribs 254 extend in a longitudinal direction at least the entire length of the infusion section of the catheter 250. Desirably, the support is constructed from a medical grade polymer, and preferably, from a nylon material.

A porous membrane 258 is wrapped around the support and preferably contacts the outward facing surfaces of the ribs 254. If desired, the membrane 258 may be secured to the ribs 254, such as with a medical grade adhesive, for example. Preferably, the membrane 258 is similar to the membrane 26 of the catheter 20 and possesses properties tending to regulate a flow of fluid through the membrane 258. Accordingly, fluid exits the infusion section of the catheter in a substantially uniform flow rate along the length of the infusion section.

The support 252 and the membrane 258 cooperate to define a plurality of lumens between adjacent ribs 254. Fluid enters the lumens 260 and exits the catheter 250 through the membrane 258, desirably at a substantially uniform rate. The provision of multiple lumens 260 enhances the membranes 258 ability to control fluid flow from the catheter 250 by insulating the fluid within each lumen 260 from having an effect on the fluid within any other lumen 260.

Preferably, the support 252 includes an external anti-microbial layer 262. As described above, the anti-microbial layer 262 preferably contains silver ions that are released into fluid within the lumens 260 to inhibit microbe growth on or within the catheter 250 and, preferably, in the area surrounding the catheter 250. If desired, the membrane 258 may also include an anti-microbial layer 264. Advantageously, the provision of the anti-microbial layer 264 on the membrane 258 facilitates the release of anti-microbial substances into the fluid delivered by the catheter 250. The membrane 258 regulates the flow of the fluid from the lumens 260 and increases the amount of time that the fluid is in contact with the anti-microbial layer 264.

The illustrated anti-microbial layer 264 is an external coating on the membrane 258. However, in an alternative arrangement, the anti-microbial layer 264 may be on the inner surface of the membrane 258 in the alternative or in addition to the external layer 264. Furthermore, although the illustrated catheter 250 includes an anti-microbial layer 262 on the support 252 and anti-microbial layer 264 on the membrane 258, it is not necessary that each layer 262, 264 be present. That is, an anti-microbial layer may be provided on only one of the support 252 and membrane 258.

Figure 24:
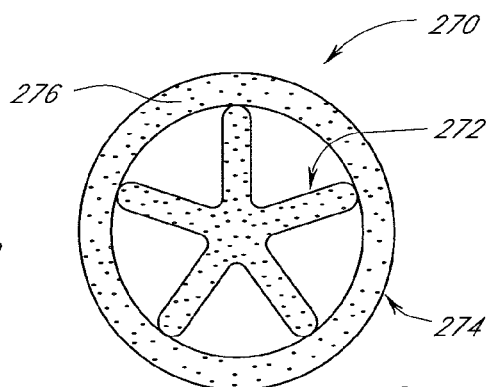
FIG. 24 is a cross-sectional view of a catheter similar to the catheter of FIGS. 1-4 and having an anti-microbial material embedded within the membrane and support.

FIG. 24 illustrates an alternative arrangement of a catheter 270 including a support 272 and a membrane 274 wrapped around the support 272. Preferably, the catheter 270 is substantially similar to the catheter 20 of FIGS. 1-4 and the catheter 250 of FIG. 23. In a preferred arrangement, the membrane 274 comprises a hollow-fiber material. The catheter 270 varies from the previously-described catheter 20 of FIGS. 1-4 in that the catheter 270 includes an anti-microbial material 276 embedded, or otherwise dispersed, within the material from which the support 272 and the membrane 274 are constructed.

As described above, the anti-microbial material 276 preferably comprises silver ions and may be introduced within the material of the support 272 or membrane 274 by any suitable method, such as an impregnation process, for example. In addition, the anti-microbial material 276 may be present within either of the support 272 or membrane 274 without being provided within the other. Furthermore, if desired, the support 272 and membrane 274 of the catheter 270 may include anti-microbial layers, similar to the layers 262, 264 of the catheter 250 described above with reference to FIG. 23.

The structure of the catheter 270 is advantageous in that the hollow fiber material of the membrane 274 provides a relatively large surface area, for a given length. As the fluid passes through the empty spaces defined by the hollow fiber membrane 274, it comes into contact with the anti-microbial material 276 within the membrane 274 and, preferably, anti-microbial substances are released into the fluid. Because of the large surface area provided by the hollow fiber, the fluid comes into contact with anti-microbial material 276 for a greater amount of time before exiting the catheter 270. This advantageous feature of the catheter 270 may apply to all of the catheters disclosed herein that incorporate a membrane.

Figure 25:
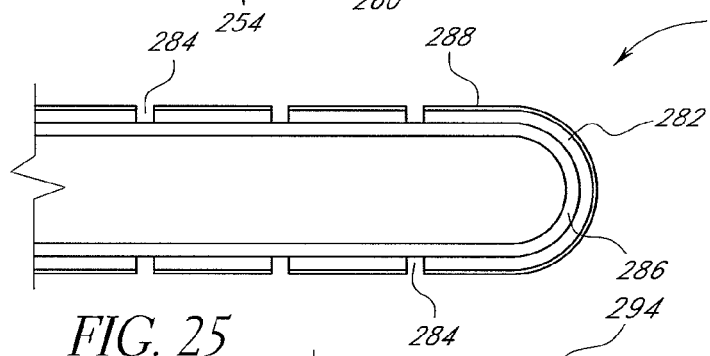
FIG. 25 is a longitudinal cross-sectional view of a catheter similar to the catheter of FIGS. 6 and 7 and having an anti-microbial layer on the catheter body.

FIG. 25 is a longitudinal cross-sectional view of a catheter 280 having uniform fluid delivery features similar to the catheters 50 and 70 of FIGS. 6 and 7, respectively. In addition, the catheter 280 preferably includes anti-microbial properties. The catheter 280 includes a tubular catheter body 282 preferably constructed from a medical grade polymer, and more preferably, is constructed from nylon. The catheter body 282 includes a plurality of exit holes 284 which together define an infusion section of the catheter 280. Within the catheter body 282 is a hollow, tubular membrane 286. The membrane 286 preferably extends at least the length of the infusion section of the catheter 280. That is, preferably, the membrane 286 covers all of the exit holes 284. Desirably, the membrane 286 also exhibits flow control properties to control a rate at which fluid passes through the membrane 286. Such flow control properties tend to regulate a flow rate of fluid through the exit holes 284, substantially as described above with reference to FIGS. 5-7. Furthermore, in the illustrated arrangement, the membrane 286 contacts the inner surface of the catheter body 282. However, in alternative arrangements, a space or gap exists between the membrane 286 and the catheter body 282, if desired.

Preferably, the catheter 280 includes an anti-microbial layer 288 on an external surface of the catheter body 282. In addition, or in the alternative, the catheter 280 may include an anti-microbial layer on the inner surface of the catheter body 282 and/or on the inner or outer surface of the membrane 286, if desired. However, providing the anti-microbial layer 288 on the exterior and/or interior surface of the catheter body 282 is desired for its relative ease of manufacture.

Figure 26:
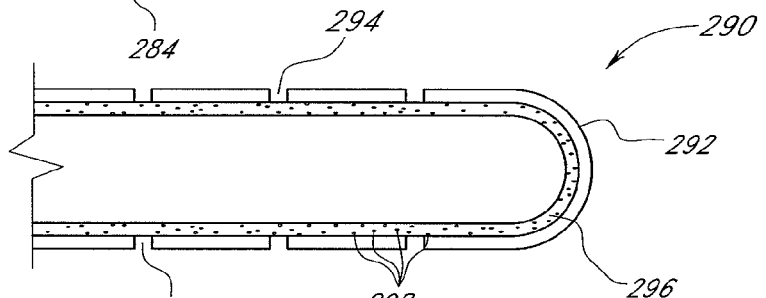
FIG. 26 is a longitudinal cross-sectional view of a catheter similar to the catheter of FIGS. 6 and 7 and having an anti-microbial material embedded within the porous membrane.

FIG. 26 illustrates a catheter 290 similar to the catheter 280 of FIG. 25. The catheter 290 includes a catheter body 292 having a plurality of exit holes 294 defining an infusion section of the catheter 290. Preferably, the catheter 290 also includes a hollow, tubular membrane 296 within the catheter body 292. Desirably, the membrane 296 contacts the inner surface of the catheter body 292 and covers the exit holes 294.

Preferably, an anti-microbial material 298 is dispersed within the membrane 296 in a manner similar to that of the catheter 270 of FIG. 24. In addition, or in the alternative, the catheter body 292 may be embedded with an anti-microbial material, depending on the degree of anti-microbial activity desired.

Figure 27:
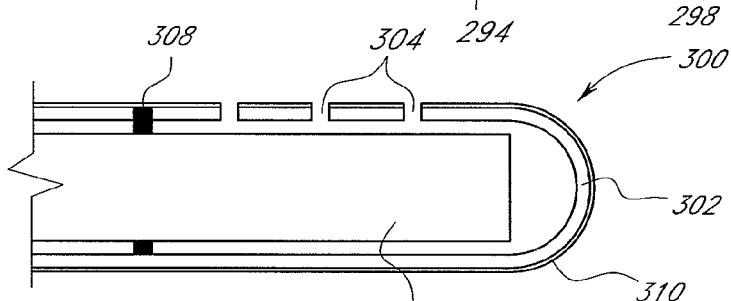
FIG. 27 is a longitudinal cross-sectional view of a catheter similar to the catheters of FIGS. 13-18 and having an anti-microbial layer on the catheter body.

FIG. 27 illustrates a catheter 300 preferably having anti-microbial properties and uniform fluid delivery properties. Preferably, fluid flow from the catheter 300 is controlled in a manner similar to the catheters described above with reference to FIGS. 13-18 to provide substantially uniform fluid flow from the catheter 300. The catheter 300 includes a tubular catheter body 302, preferably constructed from a medical grade polymer and, more preferably, constructed from a nylon material. The catheter body 302 includes a plurality of exit holes 304 that cooperate to define an infusion section of the catheter 302. Preferably, the catheter 300 also includes a generally cylindrical porous member 306 positioned within the catheter body 302. If desired, the porous member 306 may be secured to the catheter body 302 by one or more bonds 308, which may be constructed from a medical grade adhesive or other suitable arrangement, as described above with reference to FIGS. 13-18.

The catheter 300 also includes an anti-microbial layer 310 on an outer surface of the catheter body 302. If desired, however, an anti-microbial layer may be provided on the inner surface of the catheter body 302 in addition to, or alternative to, the external anti-microbial layer 310. Furthermore, the porous member 306 may include an anti-microbial layer, if desired.

Figure 28:
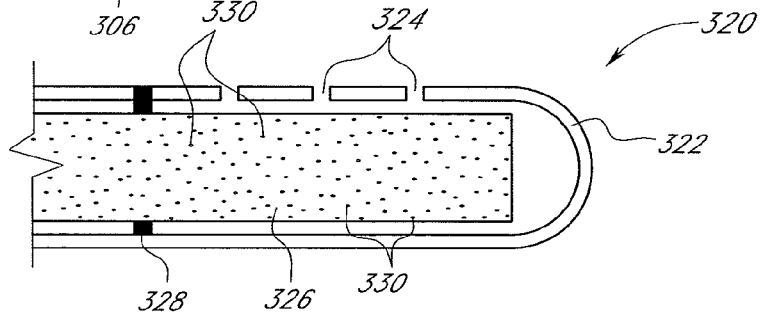
FIG. 28 is a longitudinal cross-sectional view of a catheter similar to the catheters of FIGS. 13-18 and having an anti-microbial material embedded within the porous member.

FIG. 28 illustrates a catheter 320 having fluid flow control features similar to the catheter 300 of FIG. 27 and the catheters of FIGS. 5-7. The catheter 320 includes a hollow catheter body 322 having a plurality of exit holes 324, which define an infusion section of the catheter 320. A porous member 326 is enclosed within the catheter body 322 and may be secured to the catheter body 322 by one or more bonds 328.

The illustrated arrangement includes an anti-microbial material 330 dispersed within the porous member 326. As described above, preferably the anti-microbial material 330 includes a heavy metal, and more preferably, comprises a material configured to release silver ions. Although not shown, if desired, an anti-microbial material may also be dispersed within the catheter body 322 in addition to, or alternative to, to the anti-microbial material 330 within the porous member 326. Furthermore, some components of the catheter may be coated with an anti-microbial substance and other components of the catheter may have the same or a difference anti-microbial substance embedded within the component.

Figure 29:
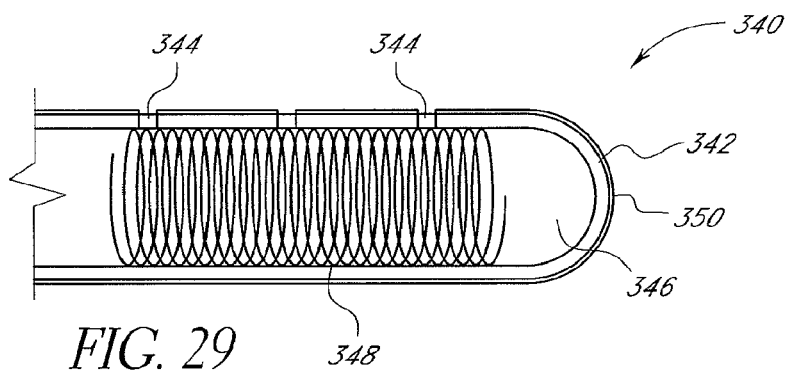
FIG. 29 is a longitudinal cross-sectional view of a catheter similar to the catheter of FIG. 11 and having an anti-microbial layer on the catheter body.

FIG. 29 is a longitudinal, cross-sectional view of a catheter 340 including anti-microbial properties and, preferably, fluid flow control properties similar to the catheter 90 described above with reference to FIG. 11. The catheter 340 includes a hollow catheter body 342, which preferably defines a plurality of exit holes 344. The exit holes 344 in combination define an infusion section of the catheter 340. Within the lumen 346 of the catheter body 342 is a coiled member 348 that preferably extends at least the length of the infusion section of the catheter 340. The coiled member 348 may be a coil spring or may be constructed of individual coil members connected together. Fluid within the lumen 346 flows between the coils of the coiled member 348 before passing through the exit holes 344.

Desirably, the coiled member 348 influences a rate of fluid flow from the lumen 346 and through the exit holes 344. In one arrangement, the coiled member 348 is a coil spring constructed of an elongate material formed into a helical shape. Desirably, the individual coils of the coil spring contact one another when the fluid within the lumen 346 is below a threshold pressure and expand once the fluid reaches a threshold pressure to permit fluid flow between the coils. However, in other arrangements, the coiled member 348 does not necessarily stretch during fluid delivery, but the fluid flow rate may instead influenced by a gap between the individual coils of the coiled member 348.

If desired, the coiled member 348 may be secured to the catheter body 342 at one or more locations. For example, the coiled member 348 may be secured to the catheter body 342 at a proximal end, a distal end, or at both the proximal and distal ends. Furthermore, the coiled member 348 may in addition, or instead, be secured at locations intermediate the proximal and distal ends. The coiled member 348 may be secured to the catheter body 342 with a medical grade adhesive, or by any other suitable method.

The illustrated catheter 340 also includes an anti-microbial layer 350 on an external surface of the catheter body 342. In other arrangements, the internal surface of the catheter body 342 may include an anti-microbial layer in addition to, or alternative to, the anti-microbial layer 350. Furthermore, if desired, the coiled member 348 may include an anti-microbial layer or an anti-microbial substance embedded within the material of the coiled member 348.

Figure 30:
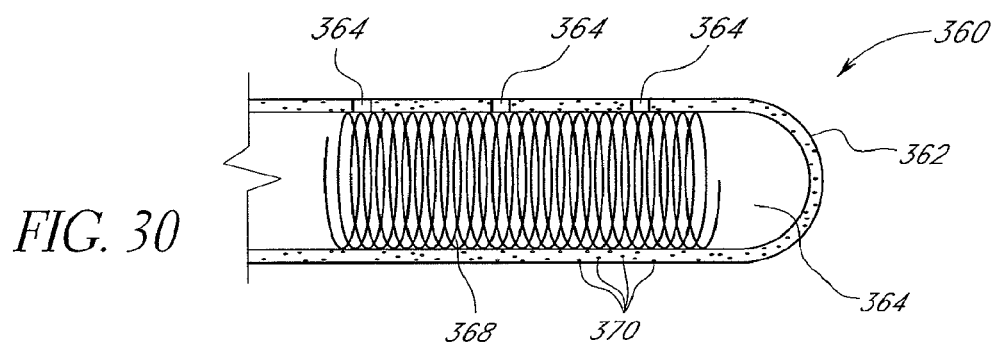
FIG. 30 is a longitudinal cross-sectional view of a catheter similar to the catheter of FIG. 11 and having an anti-microbial material embedded within the catheter body.

FIG. 30 illustrates a catheter 360 having anti-microbial properties and, preferably, fluid flow control properties similar to the catheter 340 of FIG. 29 and the catheter 90 of FIG. 11. The catheter 360 includes a hollow catheter body 362 defining a plurality of exit holes 364. Collectively, the exit holes 364 define an infusion section of the catheter 360. Within a lumen 364 of the catheter body 362, is a coiled member 368. Preferably, the coiled member 368 is substantially similar to the coiled member 348 described above with reference to FIG. 29 or the coiled member 94 described with reference to FIG. 11.

The catheter body 362 of the catheter 360 preferably includes an anti-microbial material 370 dispersed within the material from which the catheter body 362 is constructed. As described above, preferably, the anti-microbial material 370 comprises a heavy metal and, more preferably, a material containing silver ions. The silver ions preferably are configured to be released from the catheter body 362 for a sustained period into the fluid within the lumen 364 of the catheter 360 to provide the catheter 360 with anti-microbial properties.

Figure 31:
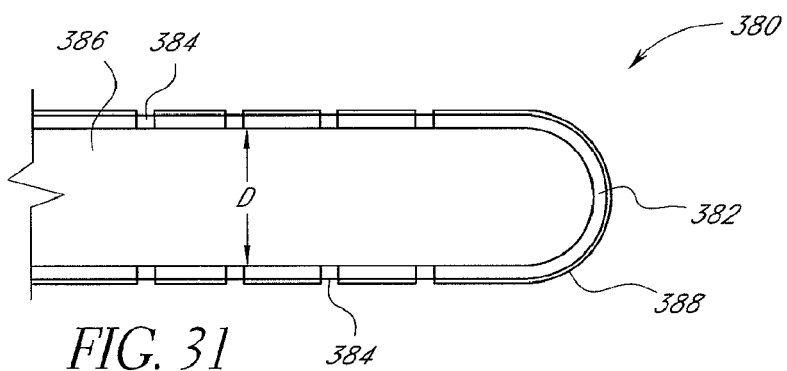
FIG. 31 is a longitudinal cross-sectional view of a catheter similar to the catheter of FIG. 12 and having an anti-microbial layer on the catheter body.

FIG. 31 is a longitudinal, cross-sectional view of a catheter 380 having anti-microbial properties and, preferably, fluid flow control properties similar to the catheter 100 of FIG. 12. The catheter 380 includes a tubular catheter body 382 defining a plurality of exit holes 384. Collectively, the exit holes 384 define an infusion section of the catheter 380. Furthermore, the exit holes 384 together define a collective exit flow area of the catheter 380. The catheter body 382 also defines a generally cylindrical lumen 386 having a diameter D. Preferably, the exit holes 384 and diameter D are configured such that a collective exit flow area defined by the exit holes 384 is less than a cross-sectional flow area defined by the lumen 386. Accordingly, the collection of exit holes 384 define a flow restricting orifice that controls a flow rate of fluid from the lumen 386 and, desirably, results in a substantially equal flow rate through each of the exit holes 384 despite the relative longitudinal position of the particular exit hole 384 along the catheter 380. Other arrangements of the exit holes 384 may also be utilized to provide desirable flow control features in addition to, or alternative to, the exit holes 384 forming a flow restricting orifice. For example, the flow area of the exit holes 384 may be configured to increase along the length of the catheter 380, similar to the catheter of FIG. 21.

The catheter 380 of FIG. 31 preferably also includes an anti-microbial layer 388 provided on an external surface of the catheter body 382. If desired, an anti-microbial layer may also be present on an inner surface of the catheter body 382 in addition to, or alternative to, the external anti-microbial layer 388.

Figure 32:
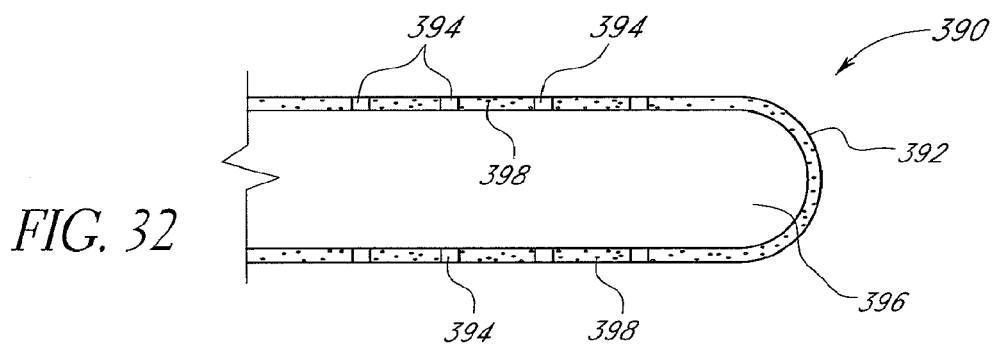
FIG. 32 is a longitudinal cross-sectional view of a catheter similar to the catheter of FIG. 12 and having an anti-microbial material embedded within the catheter body.

FIG. 32 illustrates a catheter 390 having anti-microbial properties and, preferably, fluid flow control properties similar to the catheter 380 of FIG. 31. The catheter 390 includes a catheter body 392 having a plurality of exit holes 394 preferably cooperating to define an infusion section of the catheter 390. In the illustrated arrangement, the total flow area defined by the exit holes 394 is less than a minimum cross-sectional flow area defined by the lumen 396 of the catheter 390 such that the exit holes 394 cooperate to define a flow restricting orifice.

Preferably, an anti-microbial material 398 is dispersed within the catheter body 392 such that the catheter body 392 forms an anti-microbial layer. As described above, the anti-microbial material 398 may be dispersed within the catheter body 392 by any suitable method, before or after the formation of the catheter body 392. For example, the anti-microbial material 398 may be compounded within the raw material of the catheter body 392 or the formed catheter body 392 may be impregnated with the anti-microbial material 398.

In addition to the catheters disclosed herein, it is also contemplated that other medical devices, and especially implantable medical devices, may incorporate the anti-microbial features described above. For example, it is contemplated that a catheter introducer needle may be treated with the above-described anti-microbial processes. As another example, a drain tube collar may be treated so as to possess anti-microbial properties. One exemplary embodiment of a drain tube collar is disclosed in U.S. Pat. No. 6,402,735, the entirety of which is incorporated by reference herein. One of skill in the art will be able to adapt the teachings herein to apply to other medical devices, such as the drain tube collar of the '735 patent, without undue experimentation.

FIGS. 33 and 34 illustrate another preferred embodiment of a catheter 450. As shown in FIG. 33, preferably, the catheter 450 is comprised of an elongated catheter body, or tube 454, and an outer elongated tubular porous membrane, or tubular sheath 452. The elongated tube 454 has a central lumen 468, which is in fluid communication with a fluid supply, preferably similar to the fluid supply 34 of FIG. 1.

Preferably, the tubular membrane 452 covers a length 455 of the elongated tube 454 and is positioned a distance 453 proximal of a distal end 462 of the elongated tube 454. In one embodiment, the length 455 is about 2.40 inches and the distance 453 is about 0.10 inches. In another embodiment, the length 455 is about 2.50 inches. In still another embodiment, the length 455 is about 5.00 inches. In other embodiments, the length 455 and the distance 453 may be varied so that the catheter 450 generally conforms to the particular anatomy contemplated.

As shown in FIG. 33A, desirably the tubular membrane 452 encloses a portion of the elongated tube 454 such that an annular, interstitial space 470 is created between an exterior surface of the tube 454 and an interior surface of the tubular membrane 452. In a preferred embodiment, the tube 454 is substantially concentric with the tubular membrane 452. In a preferred arrangement, the space 470 has a radial dimension of less than about 0.007 inches. In another arrangement, the space 470 may have a radial dimension of between about 0.002 and 0.007 inches. However, in some arrangements, the space 470 may be minimal, or the inner surface of tubular membrane 452 may even be in contact with a portion or all of the outer surface of the tube 454.

A plurality of fluid exit holes 466 are provided within the portion of the tube 454 enclosed within the tubular membrane 452. Preferably, the exit holes 466 are positioned throughout the entire circumference of the enclosed portion of the tube 454. The portion of tube 454 that includes the exit holes 466 defines an infusion section of catheter 450. Desirably the tubular membrane 452 is only provided along the length 455 of the infusion section. However, in an alternative arrangement, the tubular membrane could be longer than the infusion section. Also, in other embodiments, a guide wire and/or guide wire lumen may be provided to aid in the insertion of the catheter 450 into the anatomy, as will be understood by those skilled in the art.

The tube 454 may be formed from any of a variety of suitable materials, such as nylon, polyether block polyamide, PTFE, polyimide, and other materials known to those skilled in the art, giving due consideration to the goals of non-reactivity to anatomical systems, flexibility, light-weight, strength, smoothness, and safety. In a preferred configuration, the tube 454 is preferably a 19 to 20 gauge catheter tube, having inside and outside diameters of about 0.038 inches and about 0.042 to 0.045 inches, respectively.

The exit holes 466 of tube 454 are preferably about 0.015 inches in diameter and provided at equally spaced axial positions along the infusion section of the tube 454. The holes 466 preferably are arranged so that every hole is angularly displaced about 120 degrees relative to the longitudinal axis of the tube 454, from the angular location of the previous hole. The axial separation between adjacent exit holes 466 is preferably within the range of about 0.125 to 0.25 inches, and more preferably about 3/16 inch. Of course, the exit holes 466 may be provided in any of a variety of alternative arrangements. Furthermore, the infusion section of the tube 454 may have any desirable length. However, preferably the infusion section remains enclosed within the tubular membrane 452 as discussed above. The embodiment illustrated in FIGS. 33 and 34 provides a thorough, uniform delivery of fluid throughout a generally linear segment of the wound area.

The tubular membrane 452 preferably is comprised of a highly porous material. In another embodiment, the tubular membrane 452 may be made of a sponge-like or foam-like material, or a hollow fiber. The tubular membrane 452 may have an average pore size, or pore diameter, of less than about 0.23 microns so as to filter bacteria. In other arrangements, however, the pore diameter preferably is within the range of about 0.1 microns to about 0.5 microns, and more preferably within the range of about 0.2 to 0.45 microns. The tubular membrane 452 may be formed from any of a variety of suitable materials, giving due consideration to the goals of non-reactivity to anatomical systems, maintaining flexibility, fitting within the size constraints of the tubular membrane 452, and having a porosity resulting in the substantially uniform dispensation of fluid through all of the pores in the tubular membrane 452. Some suitable materials for the membrane 452 are polyethylene, polysulfone, polyethersulfone, polypropylene, polyvinylidene difluoride, polycarbonate, nylon, high density polyethylene or polytetraflouroethylene. Preferably, the tubular membrane 452 is a 19 gauge tube, having inside and outside diameters of about 0.038 inches and about 0.042 inches to 0.045 inches, respectively.

As shown in FIG. 34, preferably, the tubular membrane 452 is secured to the tube 454 by distal and proximal tubular segments, or collars 464, 465. Preferably, the tubular segments 464, 465 comprise shrink tubes that are affixed to the tube 454 and the ends of the tubular membrane 452. The tubes 464, 465 may also utilize an adhesive, such as an adhesive sold under the brand name LOCTITE, or other means known to those skilled in the art to assist in securing the tubular membrane 452 to the tube 454. Alternatively, other suitable methods may be used to secure the membrane 452 to the tube 454. For example, the membrane 452 may be secured to the tube 454 by thermal or chemical bonding, with or without the use of the tubular segments 464, 465.

In operation, the catheter 450 delivers fluid to the region of an anatomical system generally adjacent the tubular membrane 452 of the catheter 450. As the fluid flows though the central lumen 468 into the infusion section, it initially flows through the exit holes 466 and into the space 470. Fluid in the space 470 then soaks into the tubular porous membrane 452. Once the walls of the tubular membrane 452 are saturated, the fluid passes through the tubular membrane 452 and exits the catheter 450. Moreover, the fluid advantageously passes through the membrane substantially uniformly throughout the surface area of the tubular membrane 452, resulting in a substantially uniform fluid output along the length 455 of the tubular membrane 452. Thus, the fluid is delivered at a substantially equal rate throughout the wound area of the anatomy. Furthermore, this advantage is obtained for both low and high pressure fluid delivery.

In certain preferred arrangements, one or more components of the catheter 450 may employ an anti-microbial substance as described in relation to the catheters of FIGS. 23-32. For example, the inside and/or outside of the catheter tube 454 and/or tubular membrane 452 may be coated with an anti-microbial substance, or may include an anti-microbial substance embedded within the material of the particular component. Desirably, in such an arrangement, the tube 454 and/or membrane 452 are configured to release an anti-microbial agent into the fluid that may be delivered by the catheter 450, as described in detail above.

Figure 35:
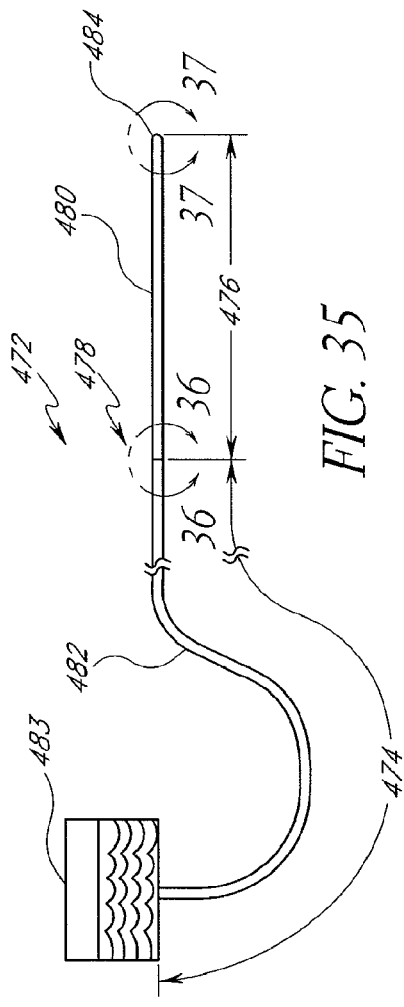
FIG. 35 is a schematic side view of a catheter having features and advantages in accordance with another embodiment of the present invention, wherein at least a portion of the catheter is constructed from a bio-absorbable material.
Figure 37:
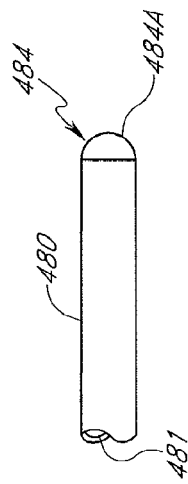
FIG. 37 is an enlarged side view of distal end of the catheter of FIG. 35.
Figure 36:
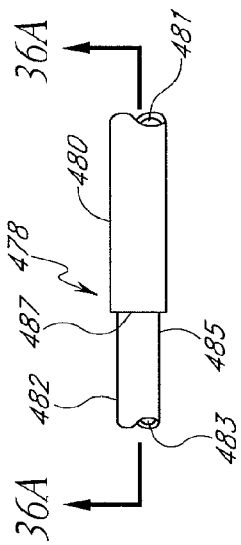
FIG. 36 is an enlarged side view of a junction between a non-porous section and a bio-absorbable section of the catheter of FIG. 35.

FIGS. 35-37 illustrate another embodiment of an infusion catheter, referred to generally by the reference numeral 472. Preferably, the catheter 472 comprises a non-porous tubular section, or tube 482, which is connected to a distal bioabsorbable, porous tubular section 480. The porous tubular section 480 has an interior lumen 481 and the non-porous tube 482 has an interior lumen 483. The non-porous tube 482 defines a non-infusing section 474 of the catheter 472, and preferably extends from a fluid supply 483 to a junction, or joint 478, as shown in FIG. 35. Similarly, the porous tubular section 480 defines an infusion section 476 of the catheter 472, and preferably extends from the junction 478 to a distal end 484 of the catheter. Preferably, the distal end 484 is defined by a tip 484*a*, which defines a distal end of the lumen 481 within the porous tubular section 480.

Figure 36A:
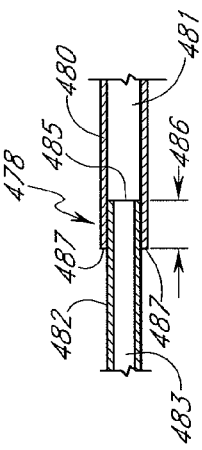
FIG. 36A is a cross-sectional view of the junction of FIG. 36, taken along line 36A-36A.

As shown in FIGS. 36-36A, preferably the junction 478 is comprised of a distal end 485 of the tube 482 being inserted into a proximal end 487 of the lumen 481 within the tubular section 480. Preferably, a suitable type of medical adhesive is applied between the overlapping surfaces of the tube 482 and the tubular section 480, to hold the tubes 480, 482 together. It is contemplated that the adhesive is of the biocompatible variety, such as medical "glue" that is used for closing wounds.

As shown in FIG. 36A, the proximal end 487 of the tubular section 480 overlaps the distal end 485 by a distance 486. The distance 486 preferably is at least about 0.02 inches. More preferably, the distance 486 is at least about 0.03 inches, though in other embodiments the distance 486 may be varied to achieve a desirable level of joint strength. The above-described overlap distances are preferred because they are capable of providing a secure joint between the tube 482 and the tubular section 480. Preferably, however, the overlap distance does not exceed about 0.25 inches so that the overlap section does not inhibit the overall flexibility of the catheter 472.

The tube 482 may be formed from any of a variety of suitable biocompatible materials, such as nylon, polyether block polyamide, PTFE, polyimide, ptfe and other materials known to those skilled in the art, giving due consideration to the goals of non-reactivity to anatomical systems, flexibility, light-weight, strength, smoothness, and safety. In one preferred embodiment, the tube 482 is comprised of a 19 gauge catheter tube, preferably having an outside diameter of no more than about 0.037 inches.

Preferably, the tubular section 480 has an outer diameter of about 0.042 inches and has an inner diameter sized so that the distal end 485 of the tube 482 fits snugly within the proximal end 487 of the lumen 481, as shown in FIG. 36A. In one preferred embodiment, the tubular section 480 is comprised of a highly porous material having an average pore size, or pore diameter, less than about 0.23 microns to filter bacteria. In other arrangements, however, the pore diameter is greater to increase the flow rate at a given fluid pressure. In such preferred embodiments, the pore diameter is within the range of about 0.1 microns to about 0.5 microns, and still more preferably the pore diameter is within the range of about 0.2 to 0.45 microns.

As used herein, a porous material, or porous membrane, desirably refers to a material or member that is configured to permit a substance to pass therethrough with at least a small amount of resistance in the area through which the substance passes. A porous material or membrane, preferably, is comprised of a material which has an inherent property, or is manipulated to attain or enhance a property, that permits a liquid to pass therethrough preferably to slow the rate of passing of the substance through the material. Alternatively, the porous material or member may slow the diffusion rate of a substance by having a pore diameter sufficiently close in size to a size of a single molecule of the substance, or a unitary grouping of molecules, to inhibit the passing of a large number of molecules, or groups of molecules, through any one pore at one time. Typically, a porous material or membrane will achieve its desired regulation of the flow of a substance as a result of micro passages through the material itself, and not as a result of distinct passages created through the material or membrane by manipulative processes such as laser drilling, for example. The distinction between a porous material or membrane and a member having a plurality of distinct holes therethrough will be readily appreciated by one of skill in the art.

In another embodiment, the tubular section 480 may be comprised of a non-porous material provided with a plurality of exit holes, as discussed herein. It is to be noted that these exit holes may be employed in the tubular section 480 in accordance with any of the embodiments discussed above. Moreover, the tubular section 480 can have any desirable length. In one embodiment, the tubular section 480 has a length of about 5 inches, and the tubular section 480 and the non-porous tube 482 have a combined length of about 20 inches. It will be appreciated that this configuration of the tubular section 480 provides uniform delivery of fluid along the length of the tubular section 480, and thus is particularly useful for delivering fluids, such as medications to a length of wound areas, such as incisions and the like. Alternatively, the catheter 472 may be configured as an aspiration catheter to remove fluids from a wound site, or other anatomic region.

The material comprising the tubular section 480, in addition to being porous, desirably is bio-absorbable, as mentioned briefly above. In one embodiment, the material comprising the tubular section 480 is dissolvable within the patient's body during a time period preferably ranging between about 5 days to about 7 days from insertion. During this period of time, the patient's body processes the bio-absorbable material such that the strength of the junction 478 is reduced. This weakening of the junction 478 facilitates detachment of the non-porous tube 482 from the tubular section 480 and subsequent removal of the tube 482 from the wound site without disturbing the placement of the remaining portion (non-absorbed portion) of the porous tubular section 480 within the wound.

The catheter 472 is particularly suitable for use in conjunction with a pain management or intravenous system (i.e., an infusion pump). In operation, a physician or other practitioner positions the catheter 472 within a wound site on a patient's body. The tubular section 480 is inserted into the wound site to such an extent that, preferably, the entirety of the tubular section 480 and a portion of the distal end 485 of the tube 482 are enclosed within the patient's body. Preferably, between about 0.1 and 0.5 inches of the distal end of the non-bioabsorbable tube 482 is enclosed within the patient. More preferably, between about 0.1 and 0.4 inches of the distal end of the non-bioabsorbable tube 482 is enclosed within the patient. The tubular section 480 may be sutured to the surrounding tissue within the wound to "tack" the catheter 472 in position. This facilitates positioning the catheter 472 precisely within the wound site. Preferably, any sutures used to tack the catheter 472 into position are also constructed from a bio-absorbable material. As a result, both the tubular section 480 and the sutures will be absorbed by the body.

Once the catheter 472 is suitably attached to the patient, a proximal end of the tube 482 may be connected to an intravenous system or other fluid supply arrangement. The catheter 472 advantageously delivers fluid or other medication to the patient over the course of 5-7 days, or longer, depending on the nature of the particular wound site in question. During this time, the tubular section 480 is absorbed by the patient's body. Once the tubular section 480 is sufficiently absorbed, and the junction 478 is weakened, the non-porous tube 482 is pulled from the wound site. Because the junction 478 is weakened, pulling on the tube 482 detaches the distal end 485 of the tube 482 from the proximal end 487 of the tubular section 480. Thus, when the tube 482 is removed, the tubular section 480 remains within the wound site and is absorbed by the patient's body.

It will be appreciated that leaving the tubular section 480 within the wound site advantageously reduces the amount of trauma imparted to the surrounding tissue that would otherwise be caused by the use and removal of a conventional catheter or pain management system. Furthermore, such an arrangement is advantageous because a small, though significant, percentage of pain management catheters break off within the patient. For example, it has been determined that approximately 0.15 percent of epidural catheters shear off, leaving a portion of the catheter within the patient. This equates to approximately 3-5 catheters per month. The implanted portion of the catheter must then be removed, resulting in undesirable trauma to the patient. With the catheter 472 as described with reference to FIGS. 35-37, the implanted portion 480 of the catheter 472 will be absorbed by the body in the event that the joint 478 separates prematurely.

In certain preferred arrangements, one or more components of the catheter 472 may employ anti-microbial substances, as described above in relation to FIGS. 23-32. For example, one or both of the tubes 480 and 482 may be coated, or embedded, with an anti-microbial substance, preferably as described above. Desirably, in such an arrangement, the tube 480 and/or 482 are configured to release an anti-microbial agent into the fluid that may be delivered by the catheter 472 or directly to the surrounding tissue, as described in detail above.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present anti-microbial catheter has been described in the context of particularly preferred embodiments, the skilled artisan will appreciate, in view of the present disclosure, that certain advantages, features and aspects of the catheter may be realized in a variety of other applications, many of which have been noted above. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims.

What is claimed is:

1. A catheter for the delivery of fluid throughout an anatomical region, comprising:
    an elongated tubular body having a closed radiused distal end defined by a continuous, unbroken distal portion of said tubular body wherein the tubular body has a constant diameter to the closed distal end, said tubular body defining an interior lumen having a minimum cross-sectional flow area, wherein the interior lumen is open and unobstructed across the constant diameter and the constant diameter used to calculate the minimum cross-sectional flow area is measured from an innermost surface of the interior lumen, a distal end portion of said tubular body including a plurality of exit holes spaced from one another along a length of said tubular body, said plurality of exit holes having a fixed, non-variable diameter such that a combined flow area of said exit holes is less than said minimum cross-sectional flow area, such that said exit holes form a flow-restricting orifice for the flow of a fluid from within said lumen through said exit holes and into said anatomical region and wherein said combined flow area defines a total exit flow area of said fluid from said catheter such that a flow rate of fluid exiting the more proximal of said plurality of exit holes is substantially equal to a flow rate of fluid exiting the more distal of said plurality of exit holes, said plurality of exit holes each defining an area equal to the other of the plurality of exit holes, said plurality of exit holes being sized such that fluid introduced into a proximal end of said lumen first flows towards said distal end portion of said tubular body and fills said distal end portion without exiting said catheter via said plurality of exit holes until a threshold pressure is reached, wherein upon reaching said threshold pressure said fluid then exits said catheter via said plurality of exit holes;
    wherein said tubular body incorporates an anti-microbial substance and is configured for the sustained release of said anti-microbial substance into said fluid;
    wherein a diameter of each of said plurality of exit holes is about 5 microns.

2. The catheter of claim 1, wherein said anti-microbial substance comprises an anti-microbial layer provided on an exterior surface of said tubular body.

3. The catheter of claim 1, wherein said anti-microbial substance comprises an anti-microbial layer provided on an interior surface of said tubular body.

4. The catheter of claim 1, wherein said anti-microbial substance comprises an anti-microbial material dispersed within said tubular body.

5. The catheter of claim 1, wherein said anti-microbial substance comprises an anti-microbial material dispersed within said tubular body and comprising a layer provided on an exterior surface of said tubular body.

6. The catheter of claim 1, wherein said anti-microbial substance comprises a metal ion selected from the group consisting of gold, platinum, silver, zinc or copper.

7. The catheter of claim 6, wherein said anti-microbial substance comprises a nanoparticle less than about 50 nm in size.

8. The catheter of claim 7, wherein the ratio of nanoparticles to base material of the treated portion of the catheter is about 600-2000parts per million.

9. The catheter of claim 1, wherein said anti-microbial substance is contained within a carrier material comprising a natural or synthetic polymer.

10. The catheter of claim 1, wherein the catheter is configured to release an anti-microbial substance at an elution rate of between about 0.8 and 3.0 µg/cm for at least the infusion section of the catheter.

11. The catheter of claim 1, wherein the catheter is configured to release an anti-microbial substance over a period of time comprising at least a first period of time and a second period of time wherein the first period of time has a first elution rate and the second period of time has a second elution rate wherein the first elution rate is greater than the second elution rate.

12. The catheter of claim 1, wherein the nanoparticles are impregnated into the catheter.

13. The catheter of claim 1, wherein the catheter has a first color before being exposed to the anti-microbial substance and a second, different color after exposure to the anti-microbial substance.

14. A catheter for the delivery of fluid throughout an anatomical region, comprising:

an elongated tubular body with a closed radiused distal end defined by a continuous, unbroken distal portion of said tubular body wherein the tubular body has a constant diameter to the closed distal end, said tubular body defining an interior lumen having a minimum cross-sectional flow area, wherein the interior lumen is open and unobstructed across the constant diameter and the constant diameter used to calculate the minimum cross-sectional flow area is measured from an innermost surface of the interior lumen, a distal end portion of said tubular body including a plurality of exit holes spaced from one another along a length of said tubular body, said plurality of exit holes having a fixed, non-variable diameter such that a combined flow area of said exit holes is less than said minimum cross-sectional flow area such that said exit holes form a flow-restricting orifice for the flow of a fluid from within said lumen through said exit holes and into said anatomical region and wherein said combined flow area defines a total exit flow area of said fluid from said catheter such that a flow rate of fluid exiting the more proximal of said plurality of exit holes is substantially equal to a flow rate of fluid exiting the more distal of said plurality of exit holes, said plurality of exit holes each defining an area equal to the other of the plurality of exit holes, said plurality of exit holes being sized such that fluid introduced into a proximal end of said lumen first flows towards said distal end portion of said tubular body and fills said distal end portion without exiting said catheter via said plurality of exit holes until a threshold pressure is reached, wherein upon reaching said threshold pressure said fluid then exits said catheter via said plurality of exit holes;

wherein said tubular body incorporates an anti-microbial substance and is configured for the sustained release of said anti-microbial substance into said fluid;

wherein a diameter of each of said plurality of exit holes is about 5 microns; and wherein said anti-microbial substance comprises a metal ion nanoparticle with a diameter less than 50 nm selected from the group consisting of gold, platinum, silver, zinc or copper.

15. A catheter for the delivery of fluid throughout an anatomical region, comprising:

an elongated tubular body with a closed radiused distal end defined by a continuous, unbroken distal portion of said tubular body wherein the tubular body has a constant diameter to the closed distal end, said tubular body defining an interior lumen having a minimum cross-sectional flow area, wherein the interior lumen is open and unobstructed across the constant diameter and the constant diameter used to calculate the minimum cross-sectional flow area is measured from an innermost surface of the interior lumen, a distal end portion of said tubular body including a plurality of exit holes spaced from one another along a length of said tubular body, said plurality of exit holes having a fixed, non-variable diameter such that a combined flow area of said exit holes is less than said minimum cross-sectional flow area such that said exit holes form a flow-restricting orifice for the flow of a fluid from within said lumen through said exit holes and into said anatomical region and wherein said combined flow area defines a total exit flow area of said fluid from said catheter such that a flow rate of fluid exiting the more proximal of said plurality of exit holes is substantially equal to a flow rate of fluid exiting the more distal of said plurality of exit holes, said plurality of exit holes each defining an area equal to the other of the plurality of exit holes, said plurality of exit holes being sized such that fluid introduced into a proximal end of said lumen first flows towards said distal end portion of said tubular body and fills said distal end portion without exiting said catheter via said plurality of exit holes until a threshold pressure is reached, wherein upon reaching said threshold pressure said fluid then exits said catheter via said plurality of exit holes;

wherein said tubular body incorporates an anti-microbial substance and is configured for the sustained release of said anti-microbial substance into said fluid;

wherein a diameter of each of said plurality of exit holes is about 5 microns;

wherein the anti-microbial substance comprises silver ions; and wherein the catheter is configured to release the silver ions over a minimum period of time comprising at least a first period of time and a second period of time wherein the first period of time has an associated first elution rate and the second period of time has an associated second elution rate wherein the first elution rate is greater than the second elution rate.

\* \* \* \* \*